(12) United States Patent
Nacouzi

(10) Patent No.: US 10,285,579 B2
(45) Date of Patent: May 14, 2019

(54) LARYNGOSCOPE

(71) Applicant: Vincent Nacouzi, Raleigh, NC (US)

(72) Inventor: Vincent Nacouzi, Raleigh, NC (US)

(73) Assignee: Vincent Nacouzi, Raleigh, NC (US)

( * ) Notice: Subject to any disclaimer, the term of this patent is extended or adjusted under 35 U.S.C. 154(b) by 459 days.

(21) Appl. No.: 14/892,632

(22) PCT Filed: May 20, 2014

(86) PCT No.: PCT/US2014/038803
§ 371 (c)(1),
(2) Date: Nov. 20, 2015

(87) PCT Pub. No.: WO2014/200674
PCT Pub. Date: Dec. 18, 2014

(65) Prior Publication Data
US 2016/0095509 A1    Apr. 7, 2016

Related U.S. Application Data

(60) Provisional application No. 61/825,368, filed on May 20, 2013, provisional application No. 61/827,177, filed on May 24, 2013.

(51) Int. Cl.
*A61B 1/267* (2006.01)
*A61B 1/008* (2006.01)
(Continued)

(52) U.S. Cl.
CPC .............. *A61B 1/267* (2013.01); *A61B 1/008* (2013.01); *A61B 1/00105* (2013.01); *A61B 1/05* (2013.01); *A61B 1/0676* (2013.01)

(58) Field of Classification Search
CPC ....................................... A61B 1/267–1/2676
See application file for complete search history.

(56) References Cited

U.S. PATENT DOCUMENTS 1,568,732 A * 1/1926 Haslinger .......... A61B 1/00098
600/196
4,295,465 A * 10/1981 Racz ..................... A61B 1/267
600/190

(Continued)

OTHER PUBLICATIONS

Nacouzi, Vincent, International Application No. PCT/US2014/038803, International Search Report and Written Opinion, dated May 12, 2014.

*Primary Examiner* — Zade Coley
(74) *Attorney, Agent, or Firm* — Taylor English Duma LLP

(57) ABSTRACT

A laryngoscope comprises a handle and an elongated blade detachably fixed to the handle. The blade includes a stationary portion having a longitudinal axis, a distal end of the stationary portion of the blade having a surface angled and upwardly and outwardly. A movable portion of the blade has a surface for engaging the tongue of the patient. The movable portion is mounted to the stationary portion of the blade for rotation about an axis substantially along the longitudinal axis of the blade. An operating member is manipulated by a user for rotating the movable portion of the blade. Laryngoscopy of a patient includes at least a rotating motion of the movable portion of the blade. In one embodiment, the laryngoscope comprises a tubular handle and an arcuate tubular blade integral with the handle.

3 Claims, 25 Drawing Sheets

(51) Int. Cl.
  *A61B 1/05* (2006.01)
  *A61B 1/06* (2006.01)
  *A61B 1/00* (2006.01)

(56) References Cited

U.S. PATENT DOCUMENTS

| | | | | |
|---|---|---|---|---|
| 4,360,008 A | * | 11/1982 | Corazzelli, Jr. | A61B 1/267 |
| | | | | 600/120 |
| 4,425,909 A | | 1/1984 | Rieser | |
| 5,498,231 A | * | 3/1996 | Franicevic | A61B 1/267 |
| | | | | 128/200.26 |
| 6,991,604 B2 | * | 1/2006 | Cantrell | A61B 1/00094 |
| | | | | 600/185 |
| 7,153,260 B1 | | 12/2006 | Girgis | |
| 2005/0054903 A1 | * | 3/2005 | Cantrell | A61B 1/00094 |
| | | | | 600/196 |
| 2007/0106121 A1 | | 5/2007 | Yokota et al. | |
| 2008/0177147 A1 | | 7/2008 | Simons | |
| 2010/0261968 A1 | * | 10/2010 | Nearman | A61B 1/00041 |
| | | | | 600/188 |

\* cited by examiner

LARYNGOSCOPE

BACKGROUND

A laryngoscope is described and shown for use in opening an airway for orotracheal intubation and, more particularly, a laryngoscope for simultaneously displacing the tongue muscle for exposing the glottis for intubating a patient with an endotracheal tube.

Oral or nasal endotracheal intubation procedures are commonly employed to secure a controlled airway and to deliver inhalant oxygen, anesthetic gases, and other therapeutic agents into the trachea and lungs of human and veterinary patients. Laryngeal exposure to visualize vocal cords and facilitate airway control through intubation is a key element in anesthesia and emergency medicine rapid sequence intubation. A laryngoscope is a key instrument for intubation procedures.

A conventional laryngoscope typically includes a handle and a blade. A proximal end of the blade is detachably connected to a distal end of the handle such that the blade extends generally normally forwardly from the handle in an L-shaped configuration. Many types of laryngoscope blades have been developed, each characterized by blade curvature, the point of such curvature, and the flange structure of the blade. The primary function of the laryngoscope in orotracheal intubation is to open the mouth and expose the larynx in order to facilitate the insertion of the endotracheal tube into the trachea. The laryngoscope blade serves to displace the tongue and allow direct visualization of the vocal cords through the mouth.

During intubation, a patient is often paralyzed with paralytic drugs or unconscious and not spontaneously breathing. With seconds or minutes to secure an airway, the patient is placed in a supine position with the head tilted backwardly. The laryngoscope blade is usually inserted laterally from the right side of the mouth in order to sweep the tongue mass to the left. The blade is directed medially or rotated slightly counter-clockwise to engage, lift and sweep the tongue away from the lumen of the pharyngeal outlet for adequate visualization of the vocal cords. The laryngoscope may be further manipulated to expose the glottic opening. In its final position, the rigid blade tip ends up angled to the left within the vallecula. The endotracheal tube is then introduced through the mouth and visually advanced, passing between the vocal cords into the subglottic space for securing the airway. Once placement of the endotracheal tube has been achieved, the laryngoscope blade is removed.

Intubation procedures involving laryngoscopy require training, skill and strength. Much of the effort goes to moving the large mass of the tongue to expose the airway and visualize the vocal cords. Unfortunately, only a small portion of the surface of the conventional blade can be used efficiently to move the tongue. In the final position, only a small portion of the blade tip engages the base of the tongue tissue, which is not effective.

Moreover, during insertion of the laryngoscope, care must be taken to avoid pressure on the teeth and gums of the patient and avoid traumatizing both the oral mucosa and the epiglottis. The process of laryngoscopy forces, at times, the users to use a levering action with the fulcrum about the teeth. This much needed levering action is usually bypassed by pulling upward on the laryngoscope handle to lift the tongue out of the visual axis. In practice, the action of displacing the tongue is also limited by the size of the mouth opening and is insufficient for sweeping aside the tongue mass, particularly in view of the distance of the tongue mass from the mouth opening. Because the laryngoscope blade is necessarily formed of a hard, inflexible material, and the manipulation awkward and challenging, dental damage is a potential result when significant pressure is exerted, which all too often is a risk when performing laryngoscopy. This is certainly accentuated in patients with difficult and narrow airways, due their neck length, body habitus, pharyngeal space opening, tongue size and other pertinent variances.

Some conventional laryngoscopes attempt to improve the practitioner's view during insertion by providing a lighted video scope or fiber optic viewing device. The video scope is carried by the laryngoscope with the objective lens located at a distal end and arranged so that the user may, via a proximal viewing end of the video scope, observe the advancement of the laryngoscope and the endotracheal tube. A camera may also be mounted in the vicinity of the distal end of the laryngoscope blade and a viewer mounted to the laryngoscope, such that the practitioner has a simultaneous line of sight and camera view during insertion. Such laryngoscopes provide for observable advance of the leading end of an endotracheal tube through the glottis and into the larynx adjacent to the vocal cords.

For the foregoing reasons, there is a need for a new laryngoscope blade for better manipulation from outside the oral cavity and for sufficiently deflecting the tongue muscle away from the glottis opening for exposing and visualizing the larynx and the vocal cords.

SUMMARY

A laryngoscope is provided for inserting into a mouth of a patient having a tongue. The laryngoscope comprises a handle and an elongate blade detachably fixed to the handle in a plane angularly disposed with respect to the longitudinal axis of the handle. The blade includes a stationary portion having a longitudinal axis. A distal end of the stationary portion of the blade has a surface angled upwardly and outwardly. A movable portion has a surface for engaging the tongue of the patient, the movable portion being mounted to the stationary portion of the blade for rotation about an axis substantially along the longitudinal axis of the blade. An operating member is manipulated by user for rotating the movable portion of the blade, wherein laryngoscopy of the patient by manipulation of the handle includes at least a rotating motion of the movable portion of the blade.

Further, a laryngoscope is provided for inserting into a mouth of a patient having a tongue. The laryngoscope comprises a tubular handle and an arcuate tubular blade integral with the handle. The blade includes a stationary portion having a longitudinal axis, and a movable portion having a surface for engaging the tongue of the patient. The movable portion is mounted to the stationary portion of the blade for rotation about an axis substantially parallel to the longitudinal axis of the stationary portion of the blade. An operating member is manipulated by the user for rotating the movable portion of the blade, wherein laryngoscopy of the patient by manipulation of the handle includes at least a rotating motion of the movable portion of the blade.

BRIEF DESCRIPTION OF THE DRAWINGS

For a more complete understanding of the present invention, reference should now be had to the embodiments shown in the accompanying drawings and described below.

FIG. 6 is a bottom plan view of the blade portion of the laryngoscope as shown in

FIG. 1

DESCRIPTION

Figure 1:
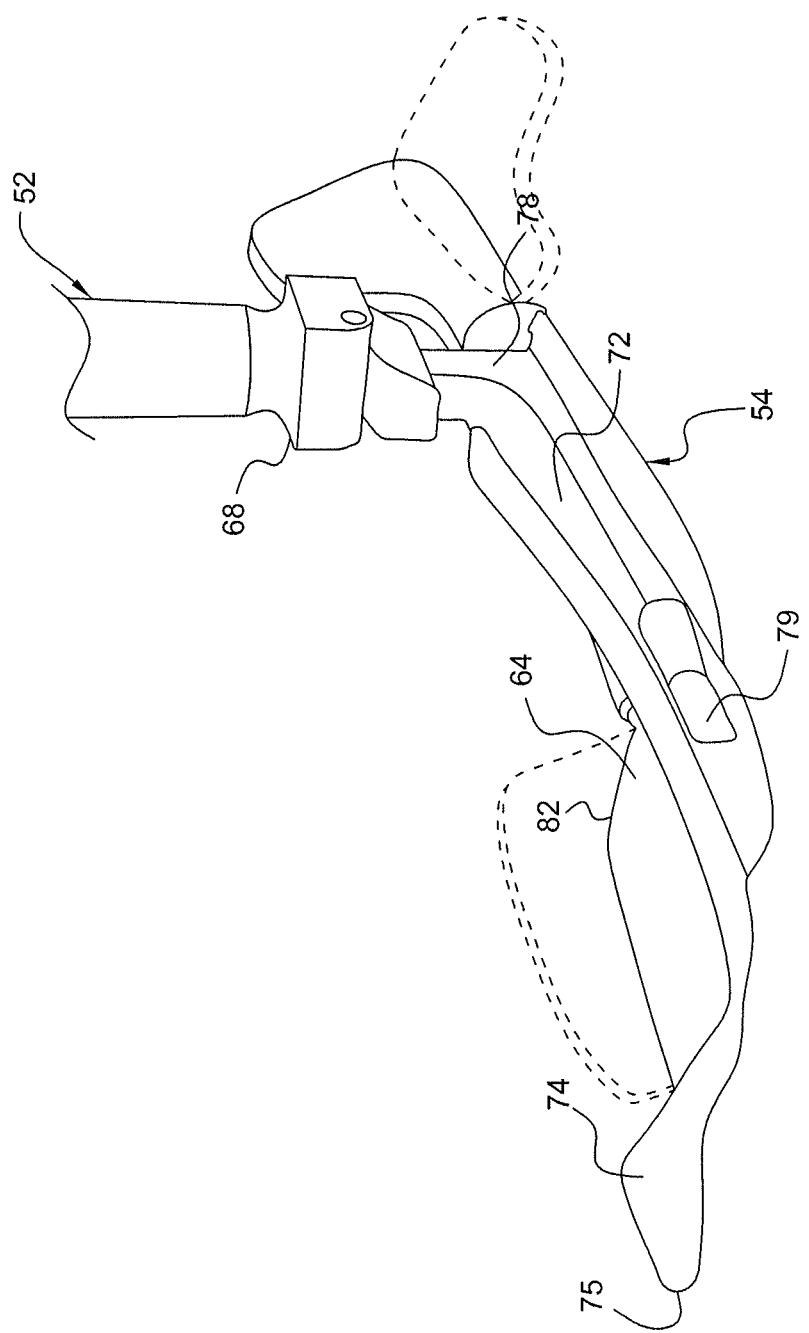
FIG. 1 is a front left perspective view of a laryngoscope with a portion of a blade shown in a first position and a second pivoted position depicted in dashed lines.
Figure 2:
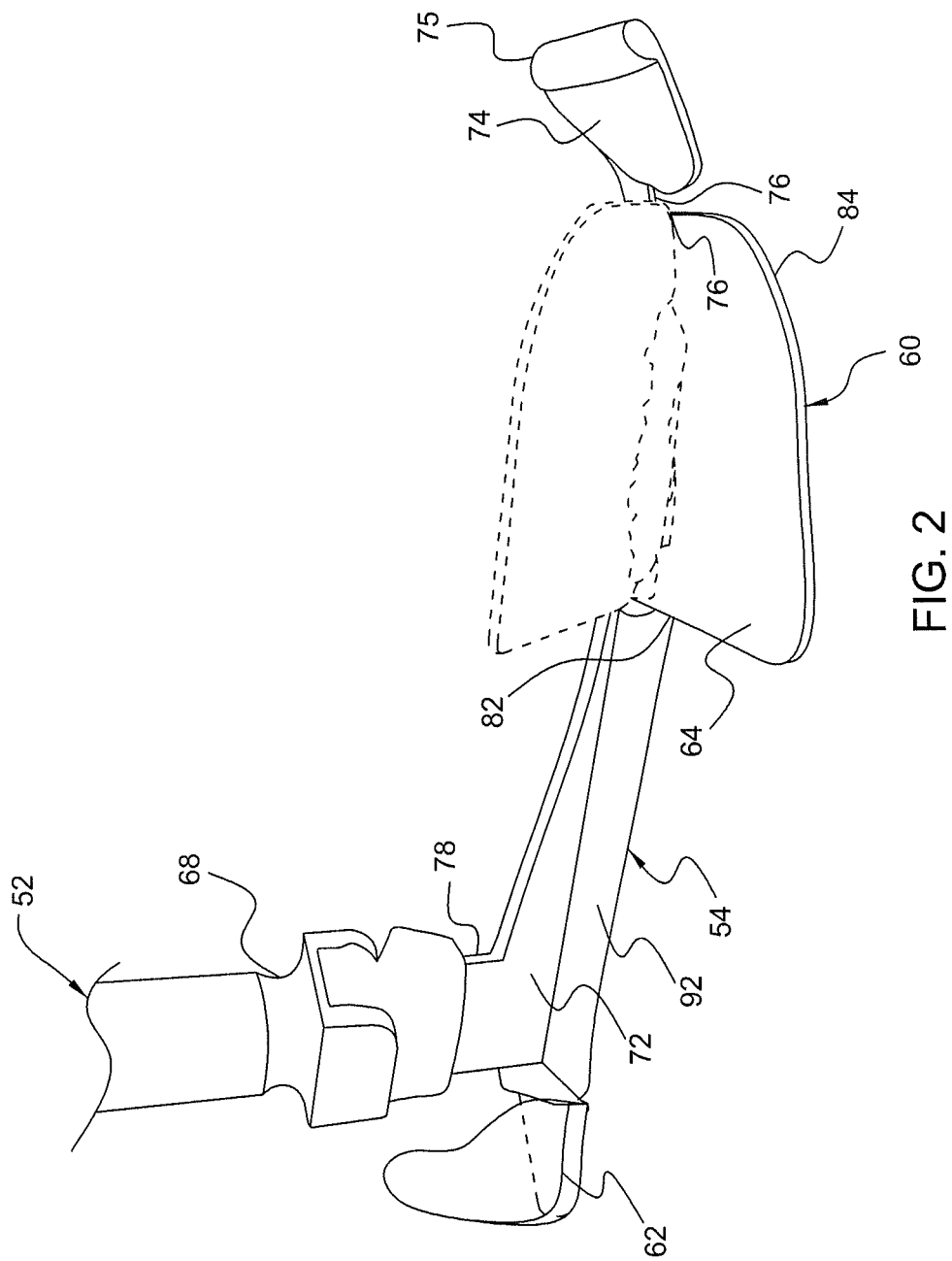
FIG. 2 is a front right perspective view of the laryngoscope shown in FIG. 1 with the portion of the blade shown in the first position and the second pivoted position depicted in dashed lines.
Figure 3:
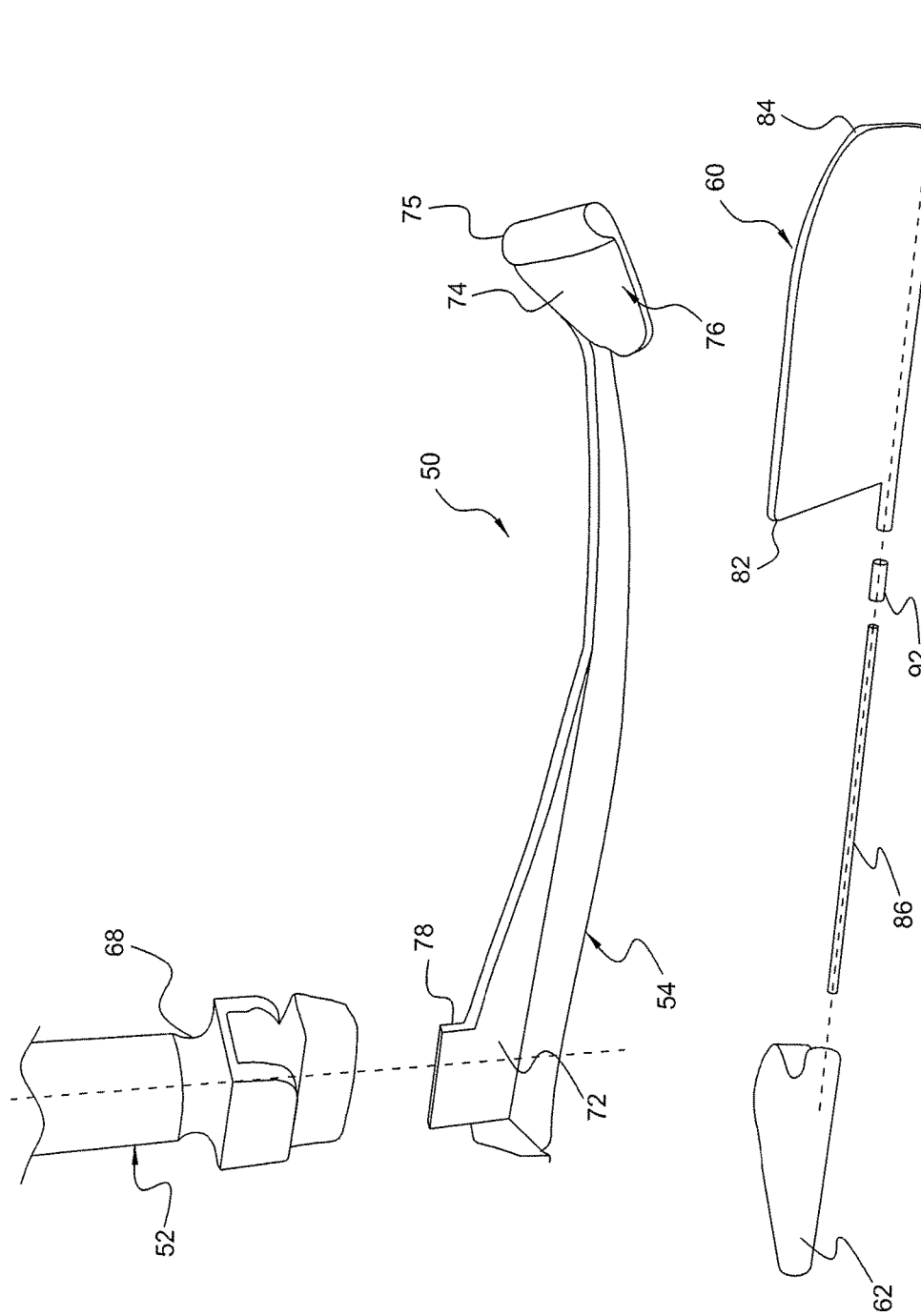
FIG. 3 is an exploded right perspective view of the laryngoscope as shown in FIG. 2.
Figure 4:
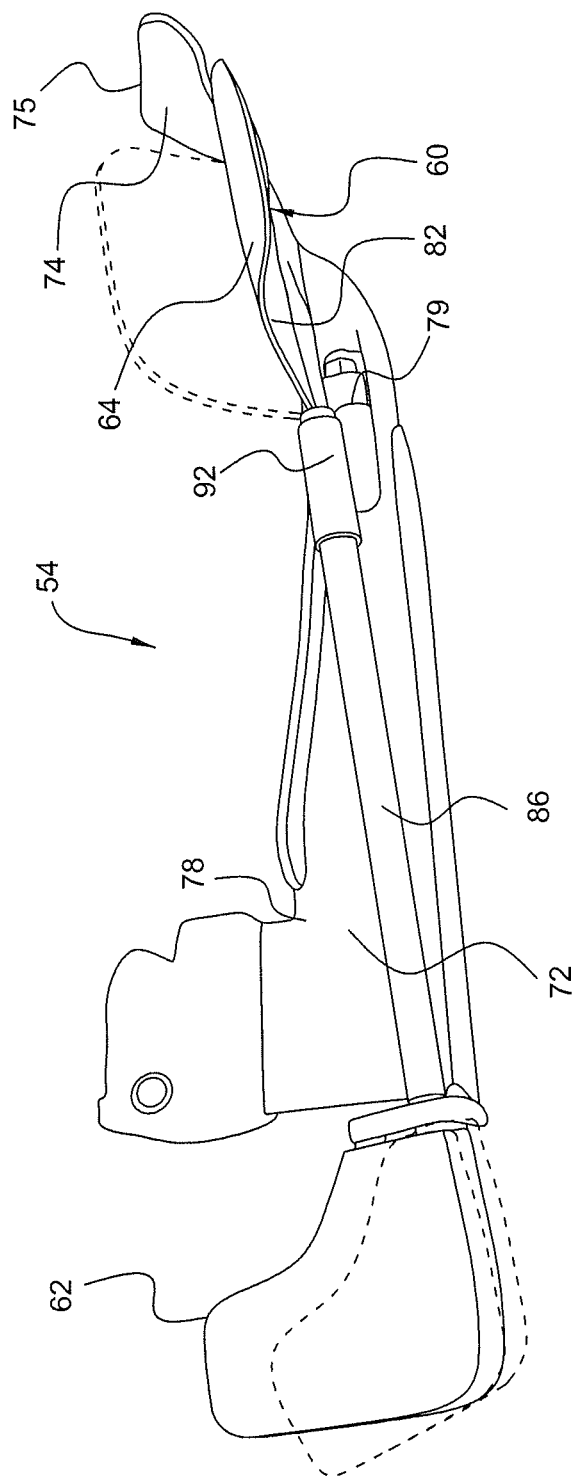
FIG. 4 is a right side elevation view of the laryngoscope as shown in FIG. 1 with the portion of the blade shown in the first position and the second pivoted position depicted in dashed lines

Certain terminology is used herein for convenience only and is not to be taken as a limitation on the invention. For example, words such as "upper," "lower," "left," "right," "horizontal," "vertical," "upward," and "downward" merely describe the configuration shown in the FIGS. Indeed, the components may be oriented in any direction and the terminology, therefore, should be understood as encompassing such variations unless specified otherwise.

Referring now to the drawings, wherein like reference numerals designate corresponding or similar elements throughout the several views, an embodiment of a laryngoscope is shown in FIGS. 1-4 and generally designated at 50. The laryngoscope 50 comprises a cylindrical handle 52, a blade 54, and a movable tongue deflector 60 pivotally attached to the blade 54. The tongue deflector 60 may be selectively angularly positioned with respect to the blade 54 by means of an operating lever 62 manipulated by the user. The lever 62 on the handle 52 can be activated by mechanical motion. Displacement of the tongue deflector 60 causes a tongue-contacting surface 64 of the tongue deflector 60 to move the tongue and expose the vocal cords and the larynx. The blade 54 and the tongue deflector 60 may be locked in their relative angular position.

The handle 52 has a proximal end 66 and a distal end 68. The handle 52 can include a power source, such as a battery, as well as other interfaces of mechanical or electrical means known to one skilled in the art.

The blade 54 comprises a substantially static portion 72. The blade 54 is formed from a substantially rigid material to allow adequate physical retraction of anatomic structures for proper use. Accordingly, the blade 54 may be constructed of metal or metal alloys that are capable of repeated use and for withstanding sterilization between uses. Suitable metal or metal alloys include stainless steel or aluminum. Alternatively, the blade 54 may be constructed of any rigid plastic that is suitable for medical use, or other low cost, sterile material, and may be provided as a single-use, disposable unit. It is understood that the blade 54 may also be made wholly, or in part, of any material known in the art.

Each end of the blade 54 may be slightly curved upward toward the handle 52. The upper major surface of the blade 54 is a tongue-contacting surface 74. Although the blade 54 is shown as slightly curved, it is understood that the blade may be more curved, or may also be provided in a substantially straight configuration.

A proximal end 78 of the blade 54 provides a standard mechanical interface for a conventional laryngoscope handle 52. The blade 54 may also provide other standard mechanical and electrical interfaces, such as wiring to a distal, miniaturized lamp 79 for illumination. Alternatively, fiber optic illumination may be employed, using fiber optic carriers within the blade 54 that may be supplied by either an external light source, or by a conventional light source contained within the laryngoscope handle 52, or by an internal lamp 79 housed proximally within the blade 54 as shown.

Figure 10:
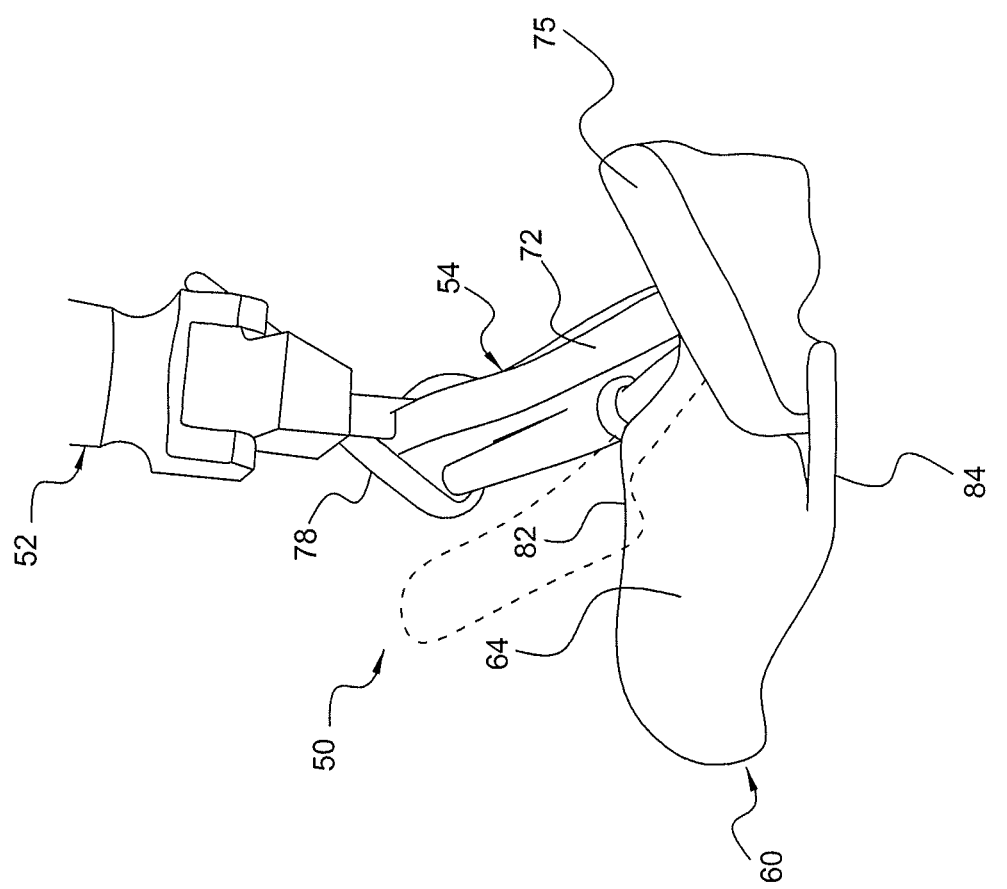
FIG. 10 is a front elevation view of the laryngoscope as shown in FIG. 1 with the portion of the blade shown in the first position and the pivoted second position depicted in dashed lines.
Figure 11:
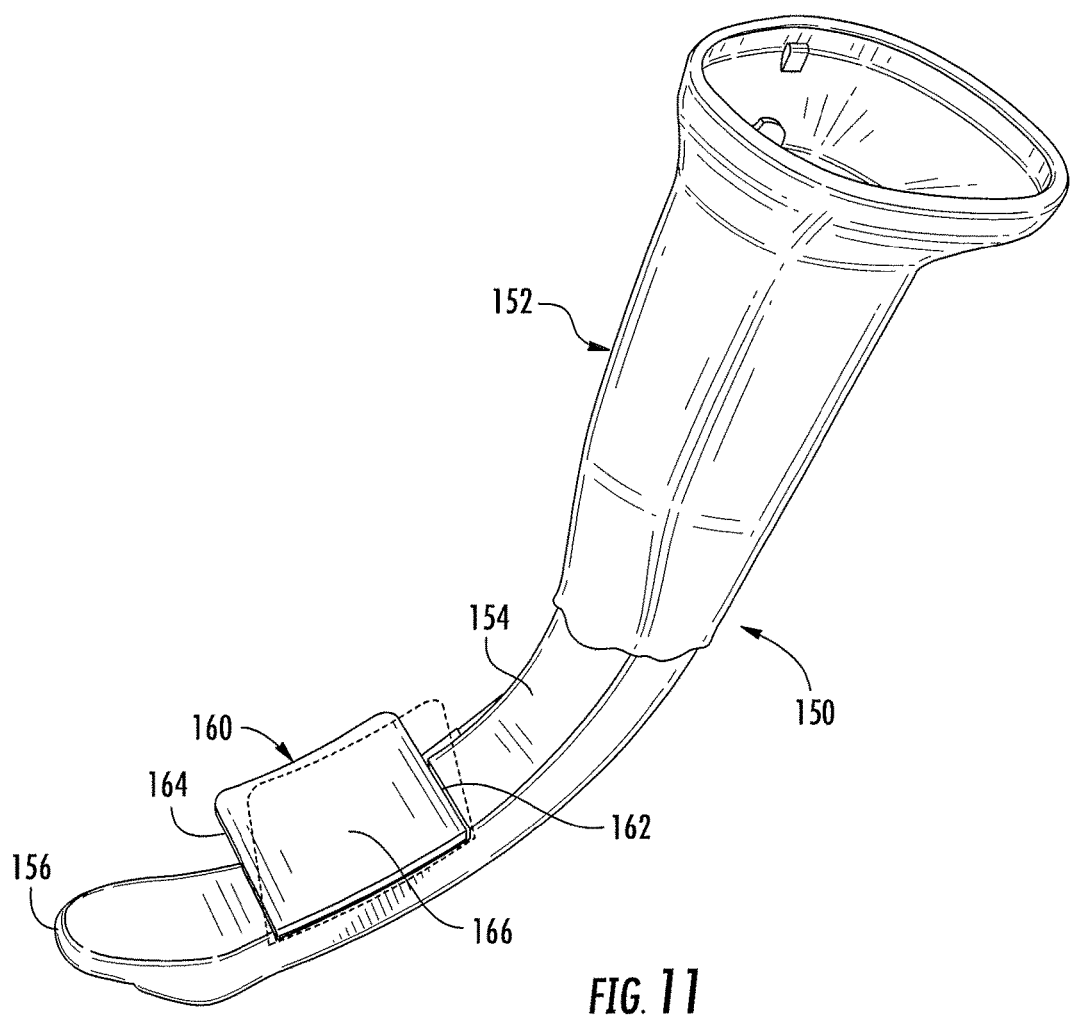
FIG. 11 is a front left perspective view of another embodiment of a laryngoscope with a portion of a blade shown in a first position and a second pivoted position depicted in dashed lines.
Figure 12:
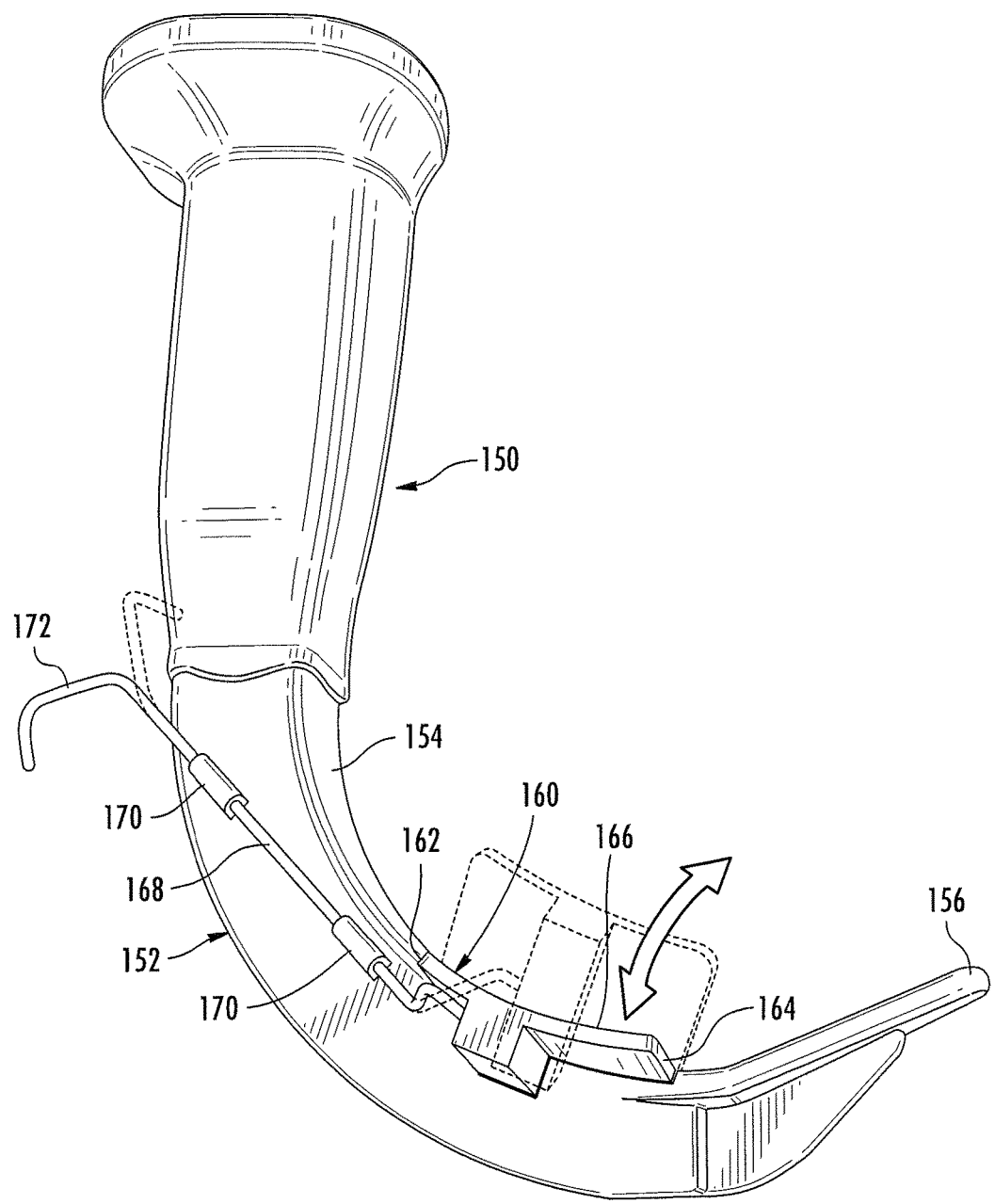
FIG. 12 is a front right perspective view of the laryngoscope shown in FIG. 11 with the portion of the blade shown in the first position and the second pivoted position depicted in dashed lines.
Figure 13:
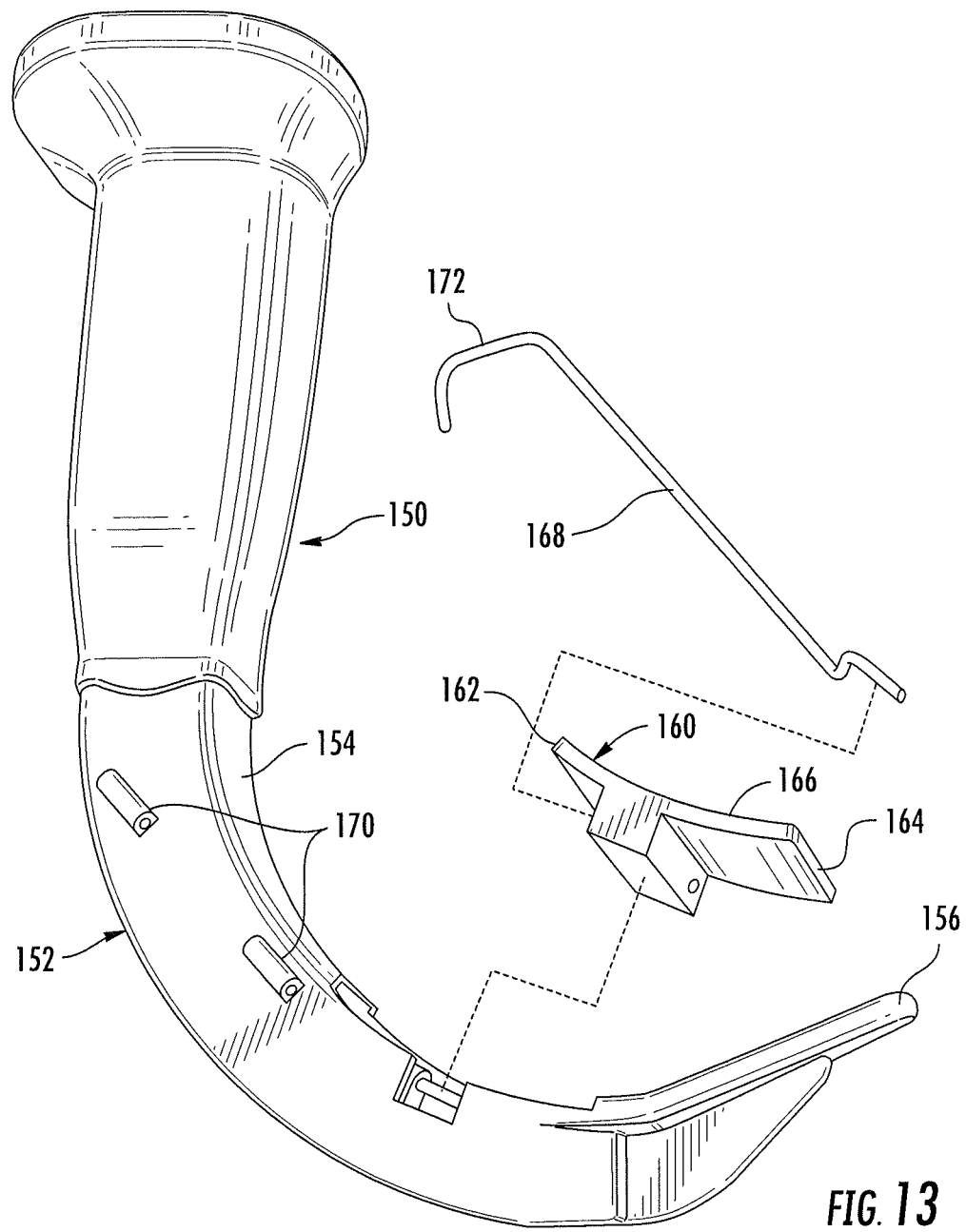
FIG. 13 is an exploded right perspective view of the laryngoscope as shown in FIG. 12.
Figure 14:
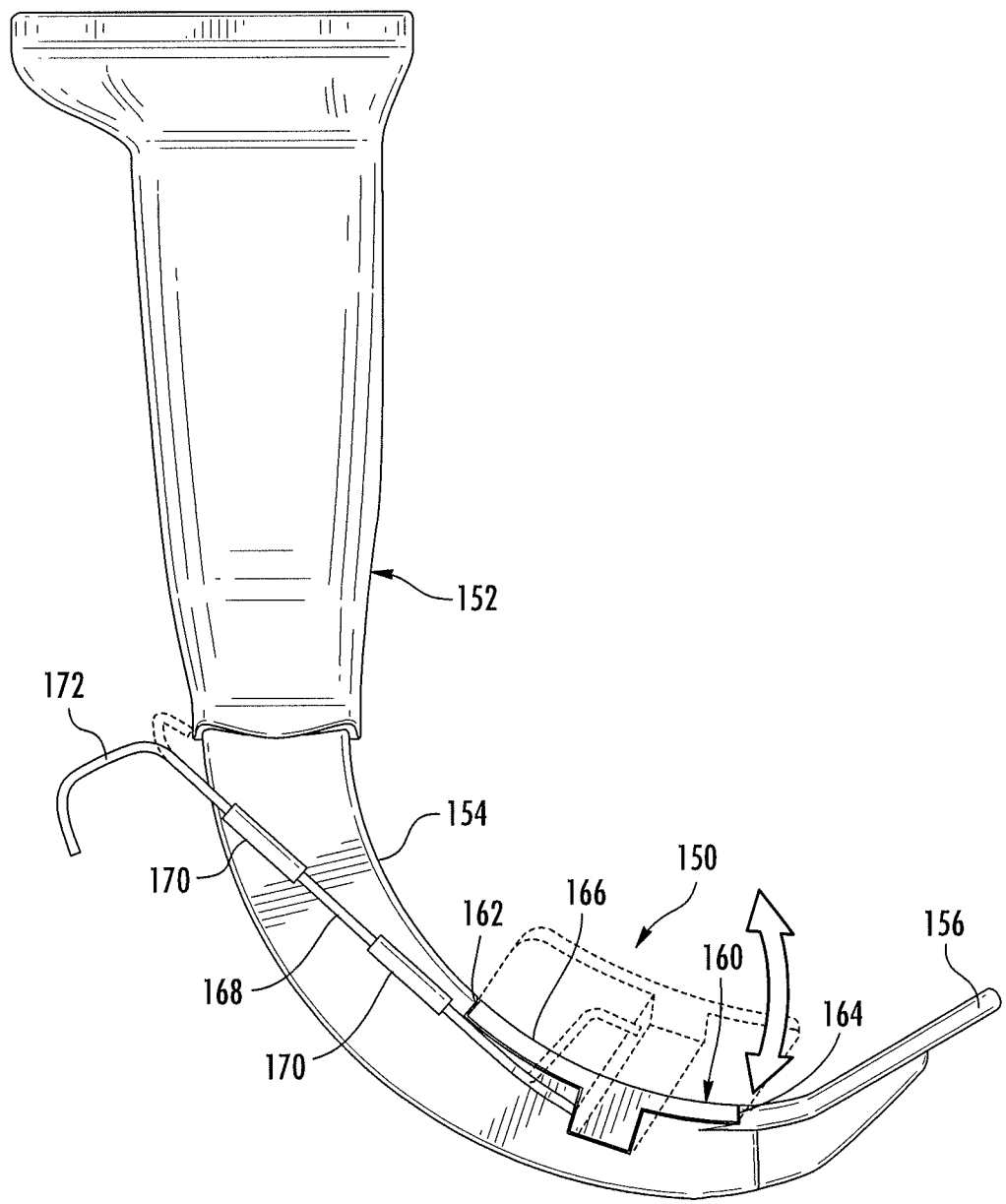
FIG. 14 is a right side elevation view of the laryngoscope as shown in FIG. 11 with the portion of the blade shown in the first position and the second pivoted position depicted in dashed lines
Figure 15:
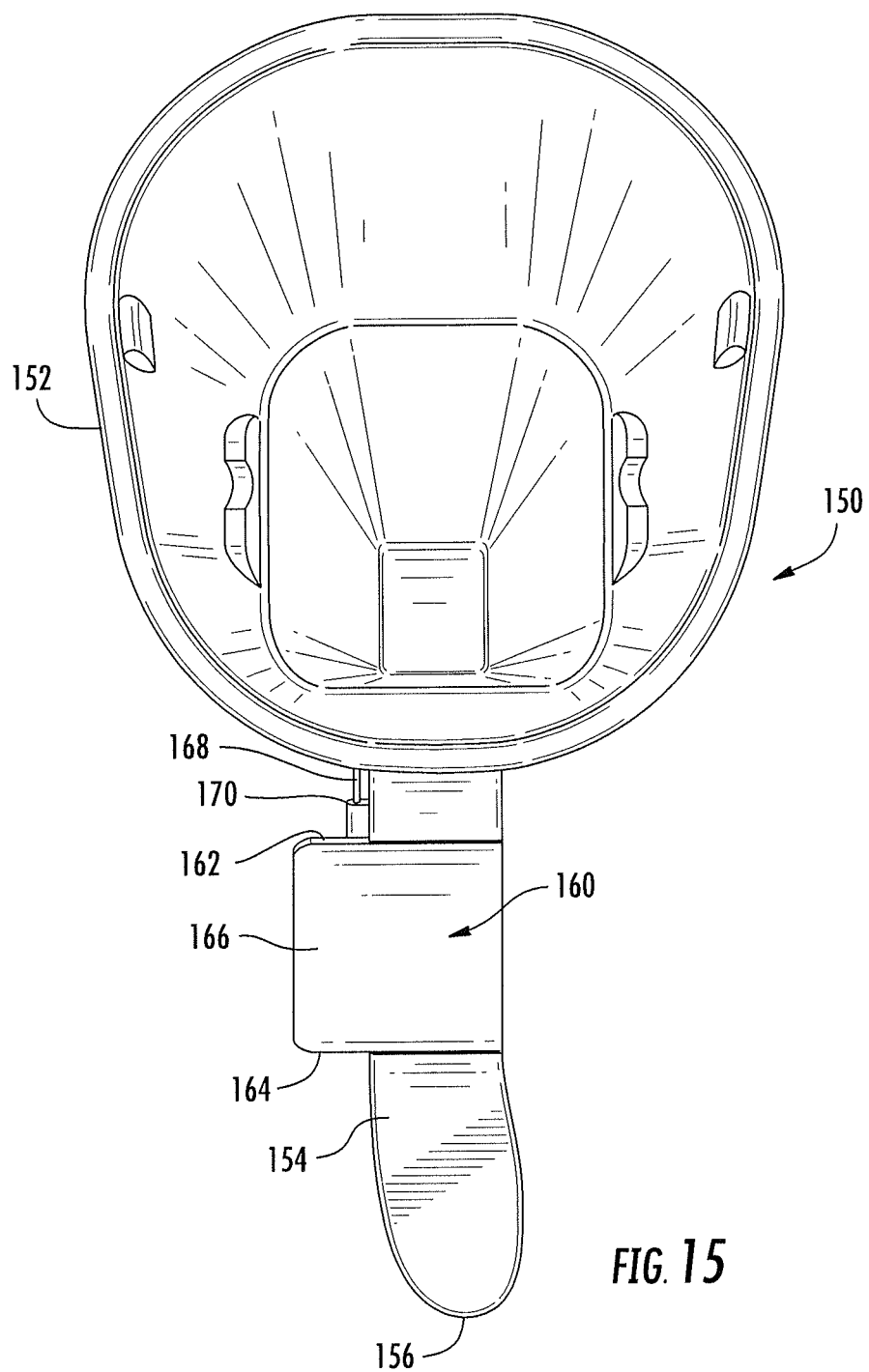
FIG. 15 is a top plan view of the blade portion of the laryngoscope as shown in FIG. 11.
Figure 16:
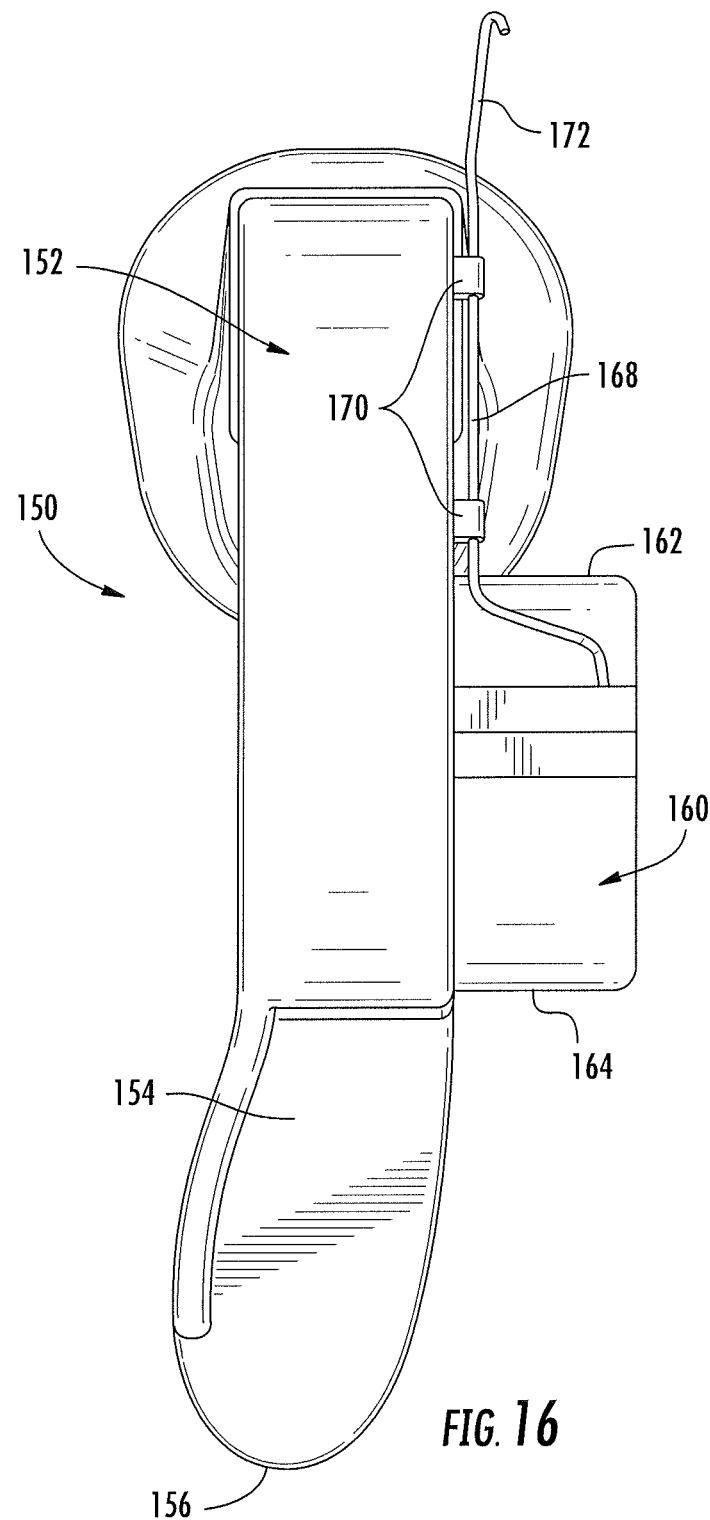
FIG. 16 is a bottom plan view of the blade portion of the laryngoscope as shown in FIG. 11.
Figure 17:
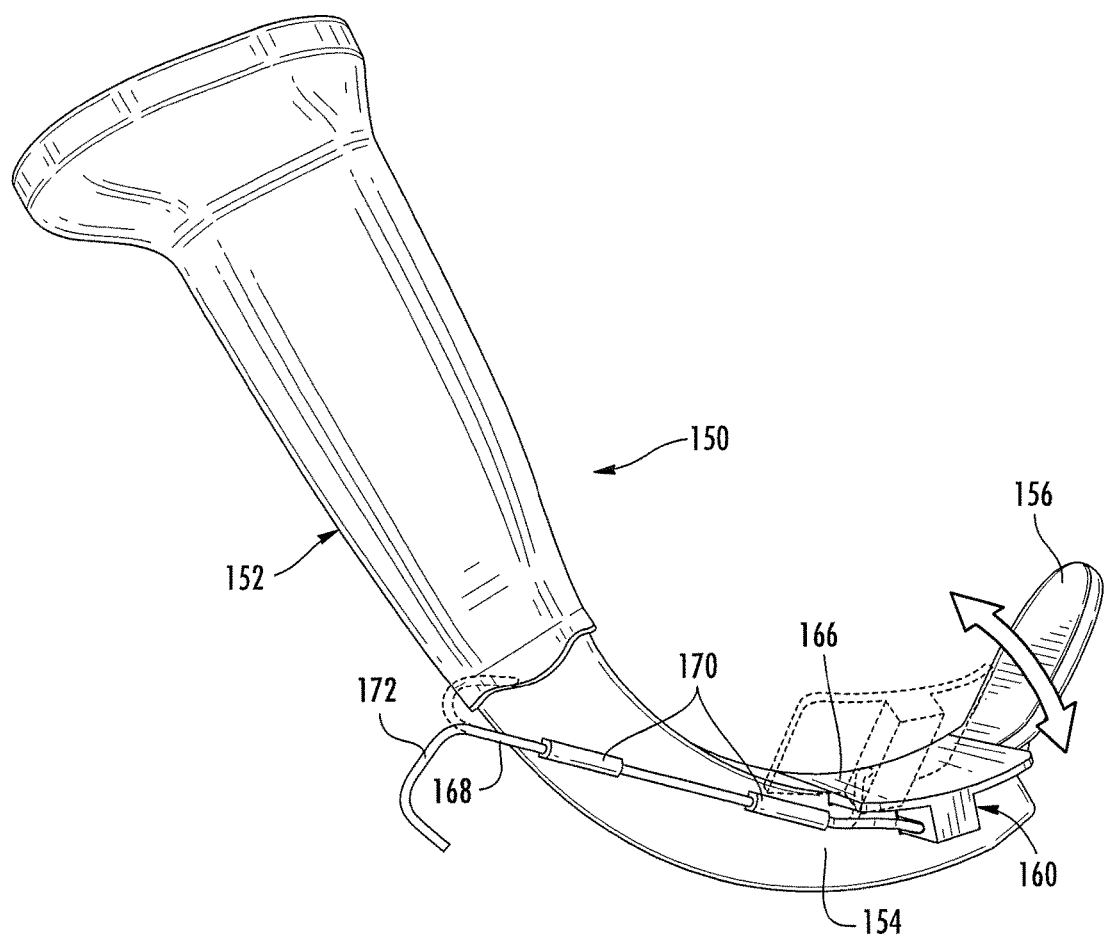
FIG. 17 is a rear right perspective view of the laryngoscope as shown in FIG. 11 with the portion of the blade shown in the first position and the second pivoted position depicted in dashed lines.
Figure 18:
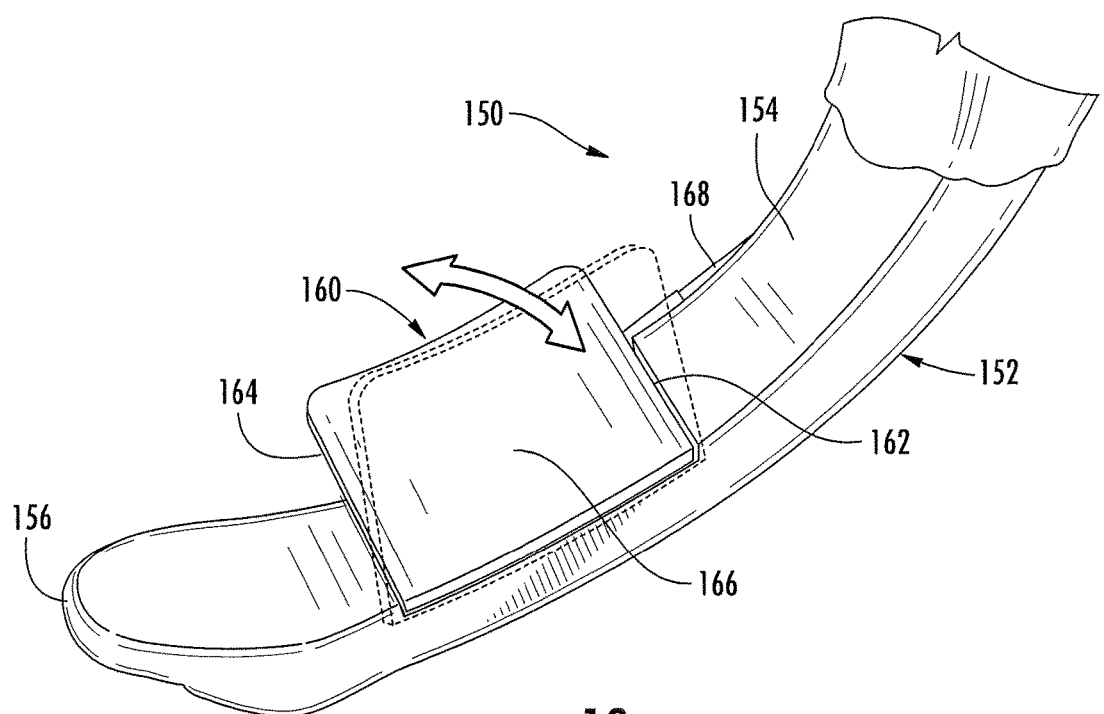
FIG. 18 is a rear left perspective view of the laryngoscope as shown in FIG. 11 with the portion of the blade shown in the first position and the second pivoted position depicted in dashed lines.
Figure 19:
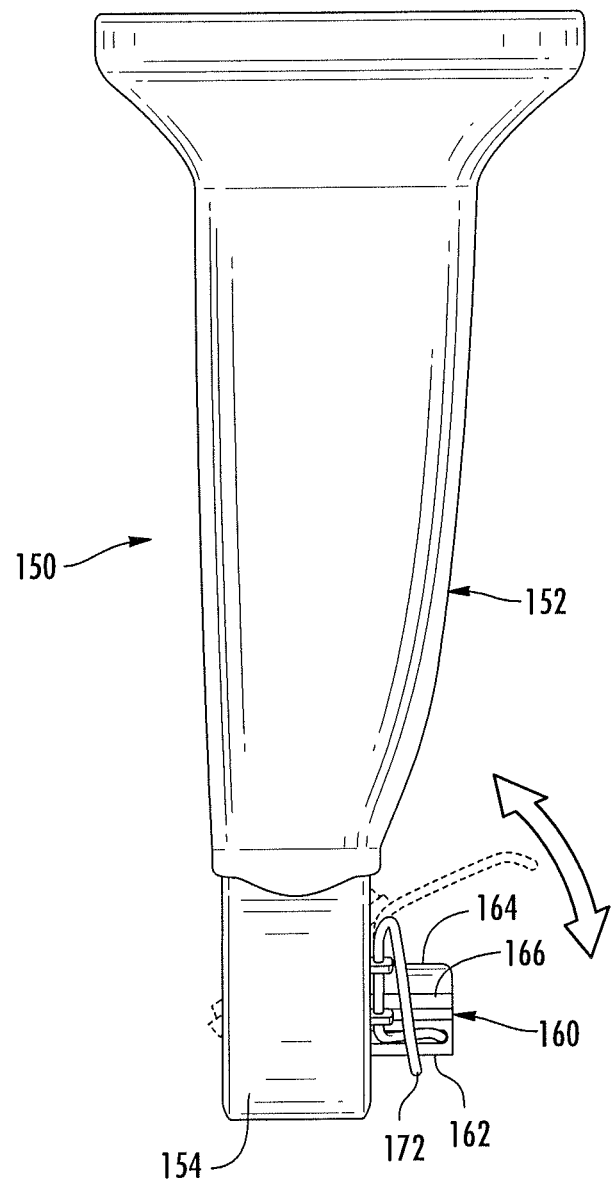
FIG. 19 is a rear elevation view of the laryngoscope as shown in FIG. 11 with the portion of the blade shown in the first position and the second pivoted position depicted in dashed lines.
Figure 20:
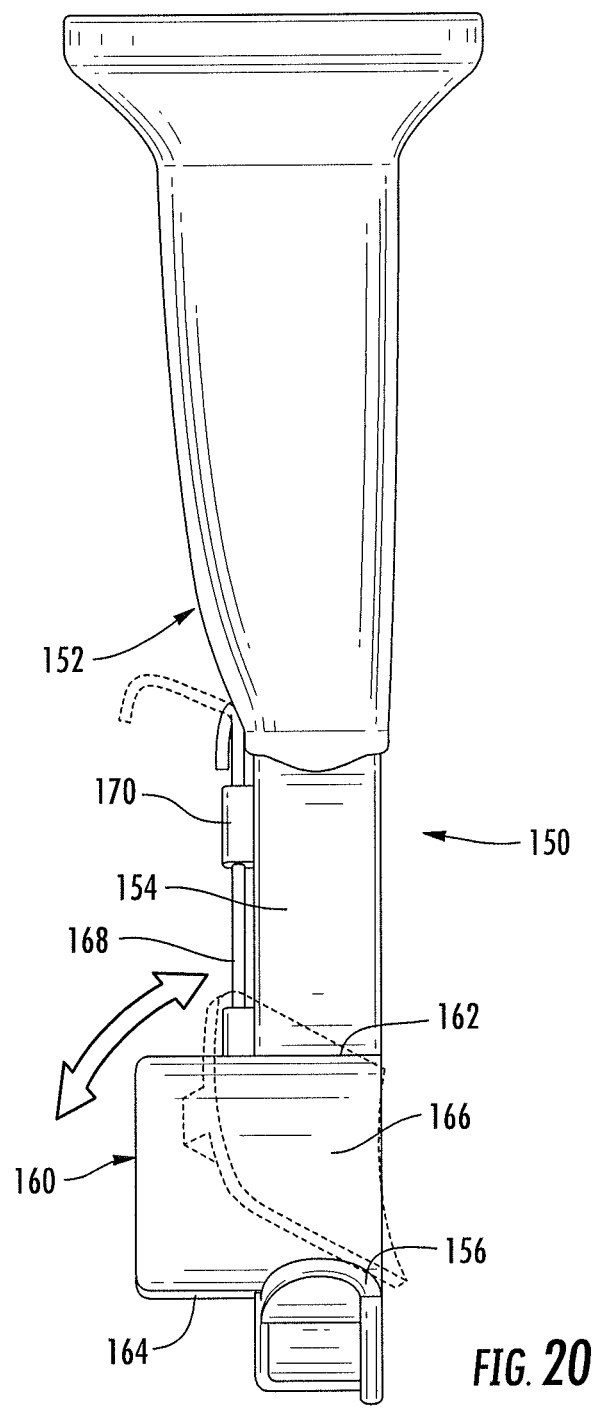
FIG. 20 is a front elevation view of the laryngoscope as shown in FIG. 11 with the portion of the blade shown in the first position and the pivoted second position depicted in dashed lines.
Figure 21:
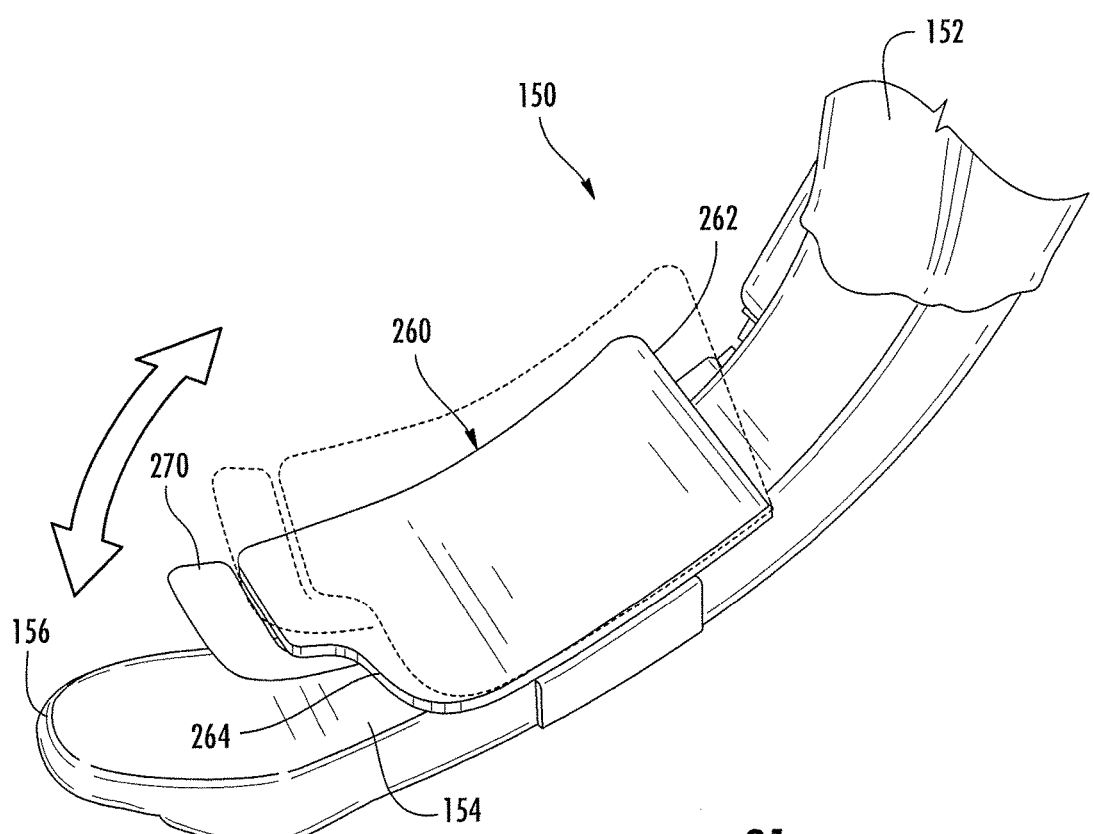
FIG. 21 is a front left perspective view of a third embodiment of a laryngoscope with a portion of a blade shown in a first position and a second pivoted position depicted in dashed lines.
Figure 22:
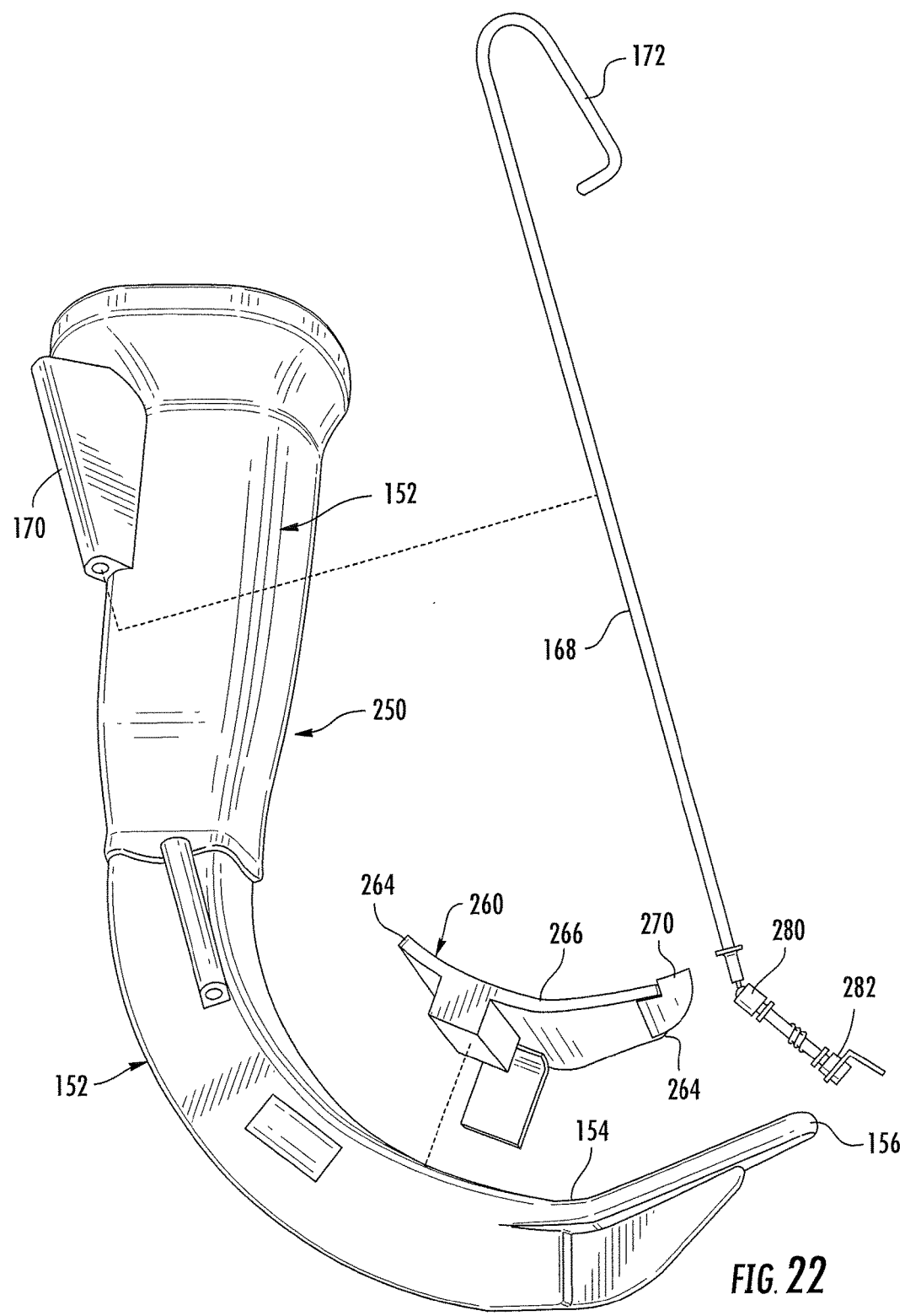
FIG. 22 is an exploded right perspective view of the laryngoscope as shown in FIG. 21.
Figure 23:
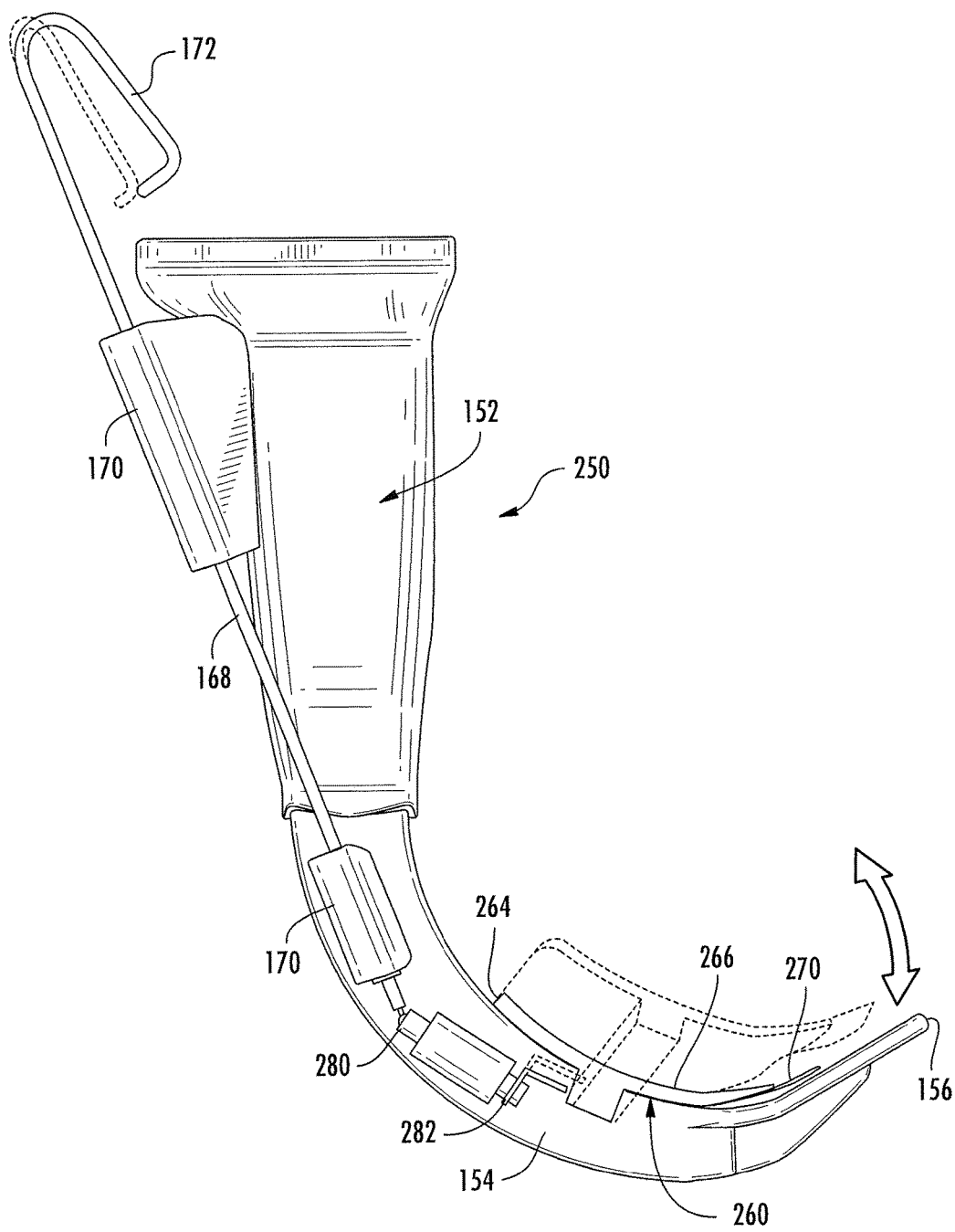
FIG. 23 is a right side elevation view of the laryngoscope as shown in FIG. 21 with the portion of the blade shown in the first position and the second pivoted position depicted in dashed lines
Figure 24:
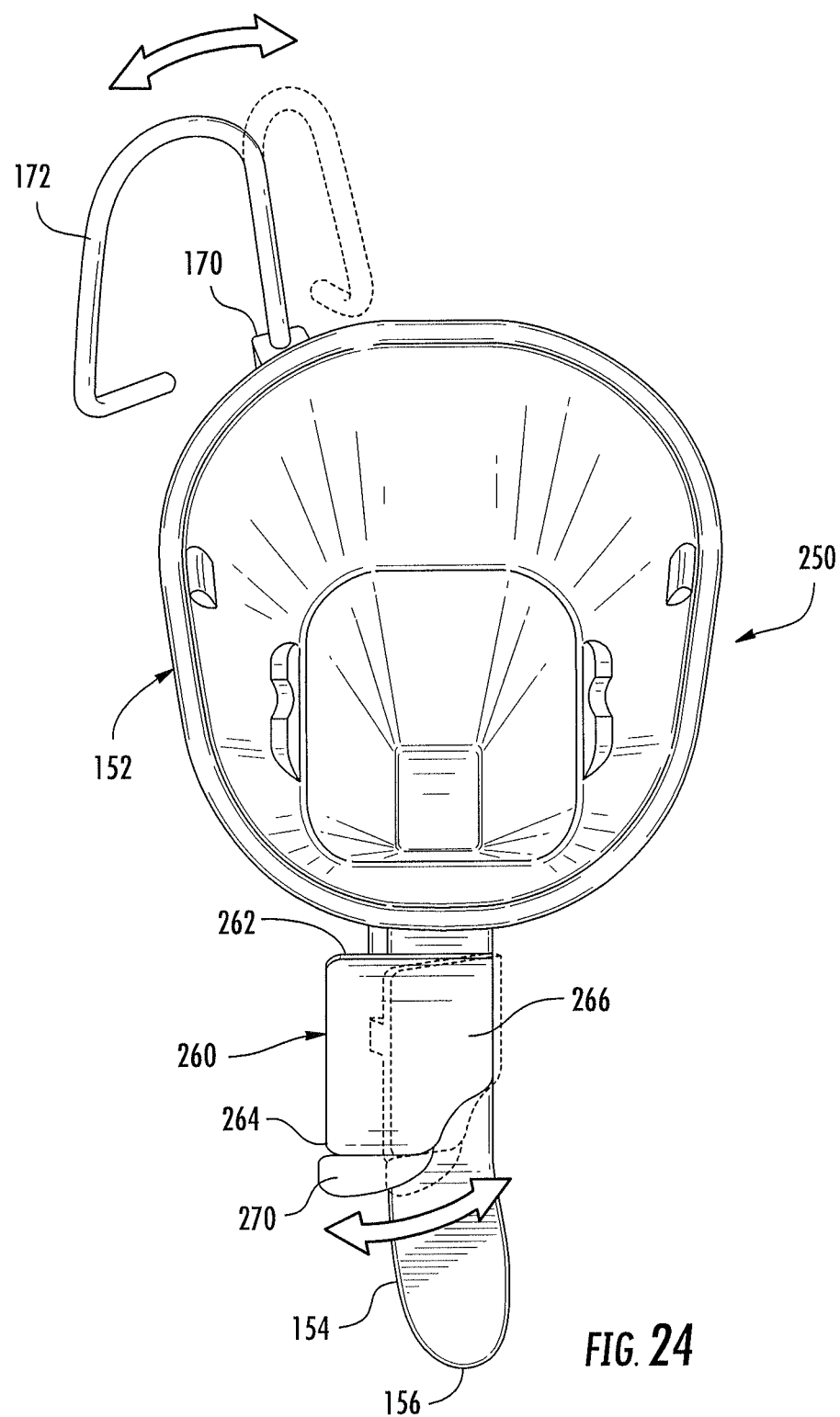
FIG. 24 is a top plan view of the blade portion of the laryngoscope as shown in FIG. 21.
Figure 25:
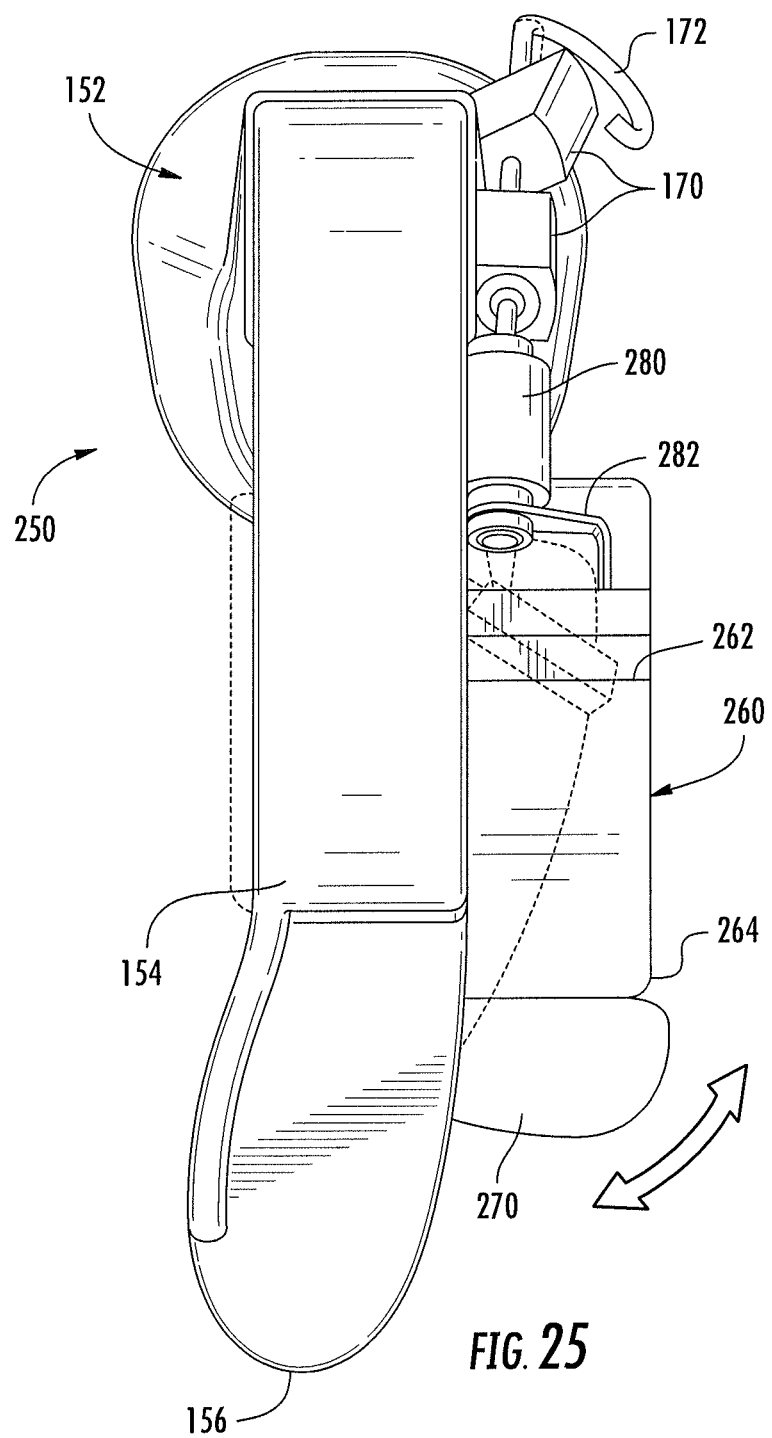
FIG. 25 is a bottom plan view of the blade portion of the laryngoscope as shown in FIG. 21.
Figure 26:
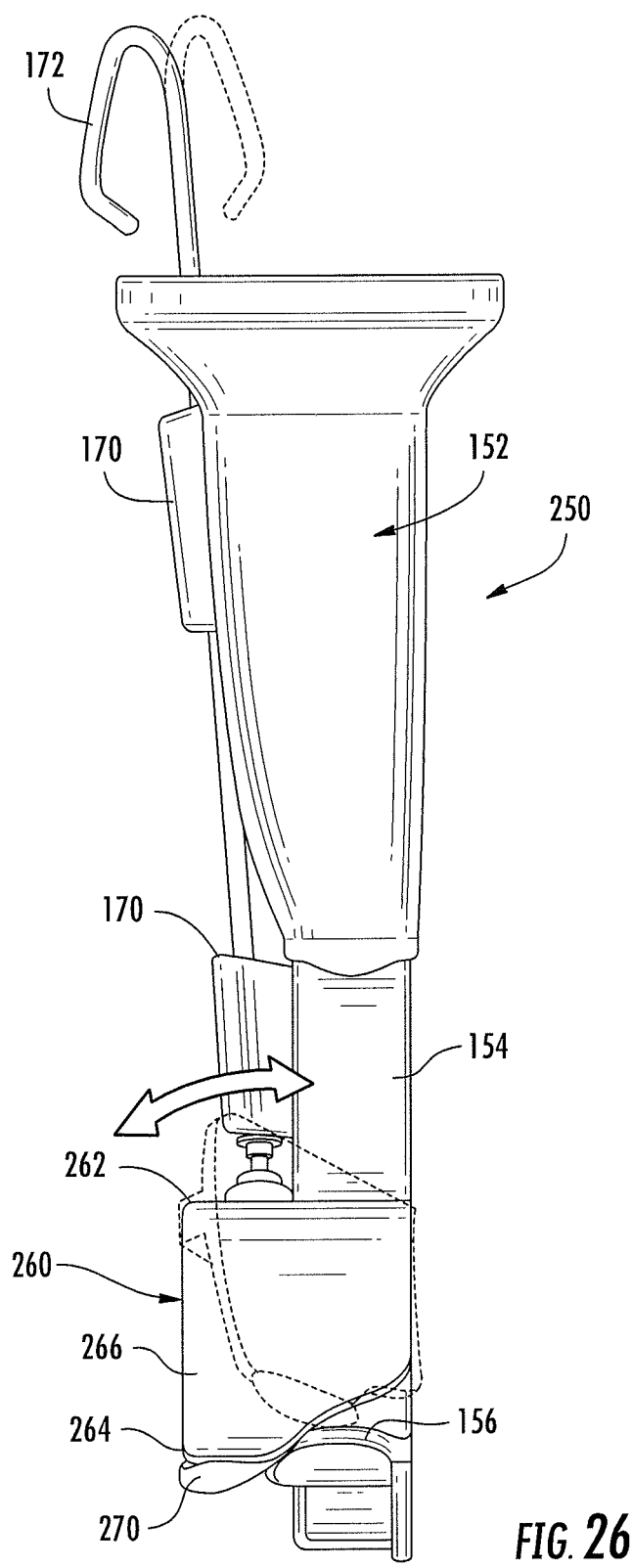
FIG. 26 is a front elevation view of the laryngoscope as shown in FIG. 21 with the portion of the blade shown in the first position and the pivoted second position depicted in dashed lines.

As best shown in FIG. 10, the distal end 75 of the blade 54 is curved upwardly and laterally away from the tongue deflector 60. The distal end 75 of the blade 54 and outer edge of the static portion 72 of the blade 54 define a transverse recess 76 intermediate the length of the blade 54 for receiving the tongue deflector 60.

As described herein above, the blade 54 is configured to functionally mount on a conventional laryngoscope handle 52 for movement with the handle. The proximal end 78 of the blade 54 may be connected to the distal end 68 of the handle 52 in a known manner. For example, the proximal end 78 of the blade 54 may be provided with an engagement hook sized and positioned to engage a transverse pivot pin of a standard laryngoscope handle 52. In one embodiment, the connected handle 52 and blade 54 define an angle of about 90 degrees, which can vary up to about 110 degrees or more in some applications. More particularly, the longitudinal axis of the handle 52 can be perpendicular to a, plane normal to the tongue-contacting surface 74 of the blade 54. When connected, the blade 54 is curved towards the handle 52. In another embodiment, the blade 54 may be attached to the distal end of the handle 52 by screw thread engagement means (not shown). Alternatively, the handle 52 and the blade 54 may be integrally formed together. The laryngoscope 50 may comprise a range of handle or blade sizes and be suitable for use with adults, children or neonates, as well as being suitable for use in veterinary practice.

The static blade portion 72 may also carry, or be adapted to provide, lighting means such as are known in the art for directing light at or toward the distal end 75 of the blade 54. For example, arrangements providing fiber optic cables or lamps, or lamps and light conducting blades are known. As described herein above, in this arrangement the blade 54 may interlock with the handle 52 in such a way as to make mechanical and electrical communication with the handle.

Figure 5:
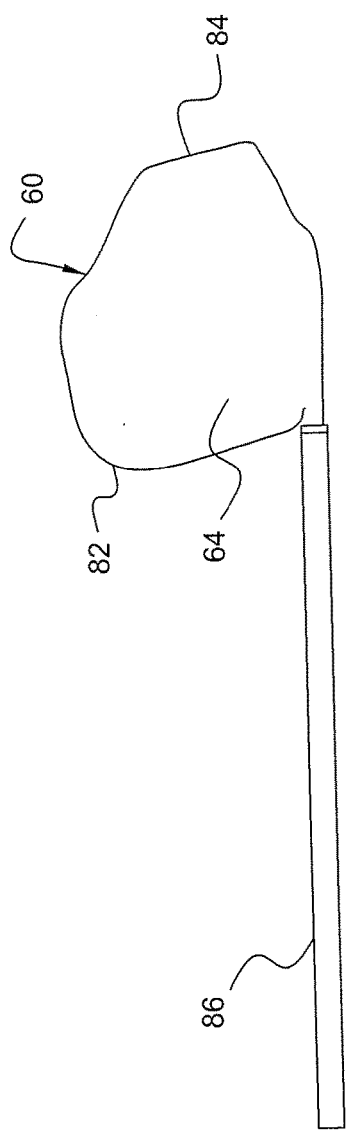
FIG. 5 is a top plan view of the blade portion of the laryngoscope as shown in FIG. 1
Figure 6:
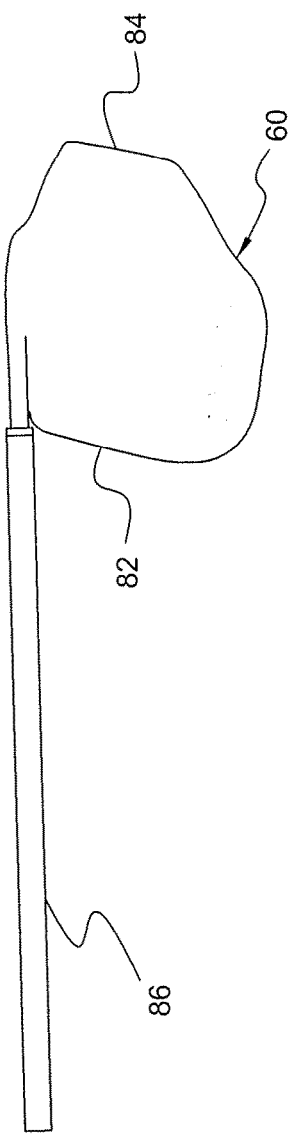

Referring to FIGS. 5 and 6, the tongue deflector 60 has a proximal end 82 and a distal end 84 and is generally planar along its length. The proximal end 82 of the tongue deflector 60 is wider than the distal end 84 of the tongue deflector 60, with the outer edge tapering inwardly to the distal end 84 from a point intermediate the length of the tongue deflector 60. The distal end 84 of the tongue deflector 60 is configured to be received, at least partially, in the recess 76 in the blade 54 such that the tongue deflector 60 extends in a substantially smooth transition into the distal end 75 of the blade 54. Specifically, in a first, home position of the tongue deflector 60, the distal end 84 of the tongue deflector 60 is flush with the corresponding adjacent edges of the blade 54 and the distal end 75 of the blade 54 defining the recess 76. The tongue deflector 60 is configured so that the tongue-contacting surface 74 of the tongue deflector 60 is substantially flush with the upper surface of the blade 54. The tongue contacting surface 64 of the tongue deflector 60 is shaped so as to provide surface continuity with the blade 54 when the tongue deflector 60 is in the home position. In this arrangement, the tongue deflector 60 provides no greater bulk that might obstruct either the visual field or working access distal to the tongue deflector 60 during an intubation procedure.

The tongue deflector 60 is pivotally mounted to the blade 54 so that the tongue deflector 60 can pivot relative to the blade 54 to execute a tongue deflecting movement for exposing the glottis, the opening portion of the larynx containing the vocal cords. More particularly, a rod 86 is fastened along the inner edge of the inner surface of the tongue deflector 60 for rotation with the tongue deflector 60. The rod 86 is journaled in at least one tubular sleeve 92 fixed to the inner surface of the blade 54. This arrangement allows the tongue deflector 60 and the rod 86 to pivot freely with respect to the blade 54 about a rotation axis. The tongue deflector 60 can thus articulate, which means movement upward, downward, or in a circular or elliptical path, along or about the axis of rotation. It is understood that in one embodiment the rod 86 or the tongue deflector 60 can be spring-biased to return the tongue deflector 60 to the home position. It is further understood that the tongue deflector 60 may be pivotally mounted to the blade 54 by any conventional means, such as ball and socket joints, hinges, straps, and the like.

Figure 7:
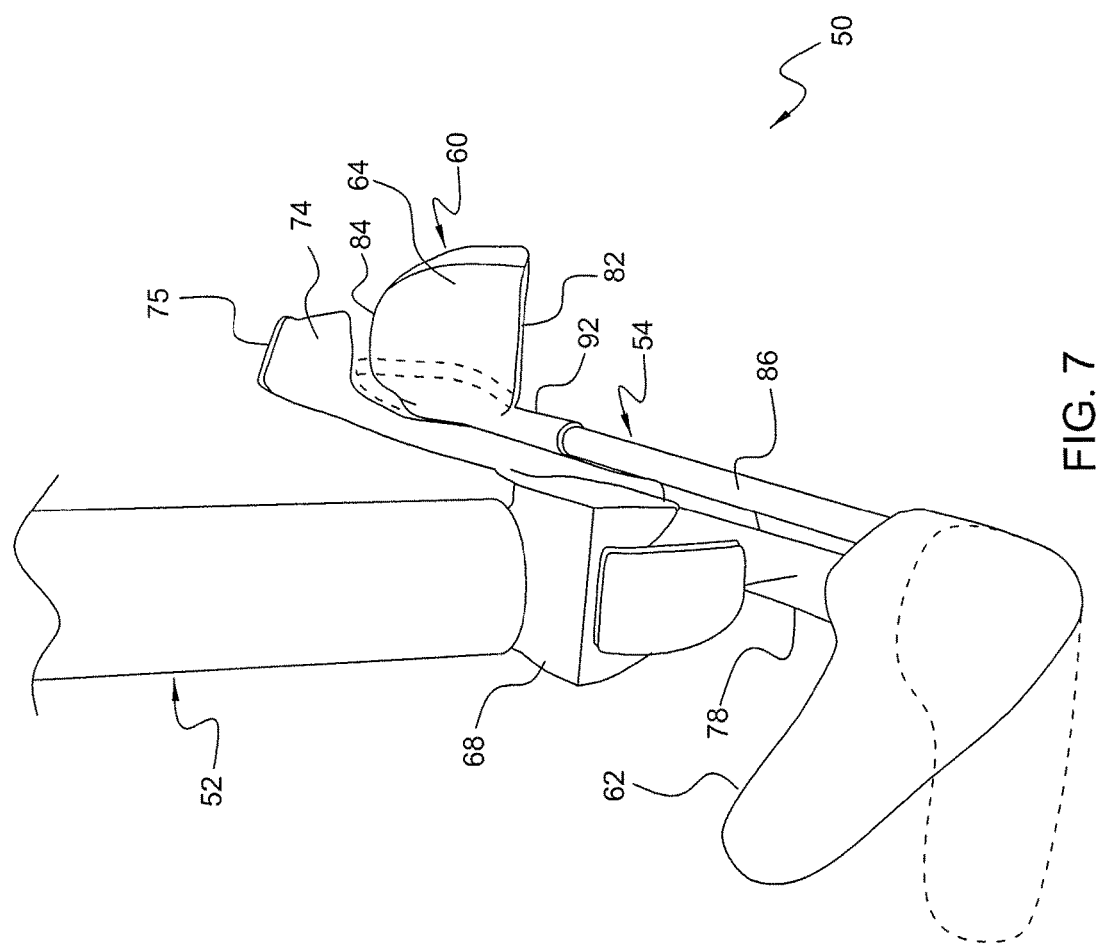
FIG. 7 is a rear right perspective view of the laryngoscope as shown in FIG. 1 with the portion of the blade shown in the first position and the second pivoted position depicted in dashed lines.
Figure 8:
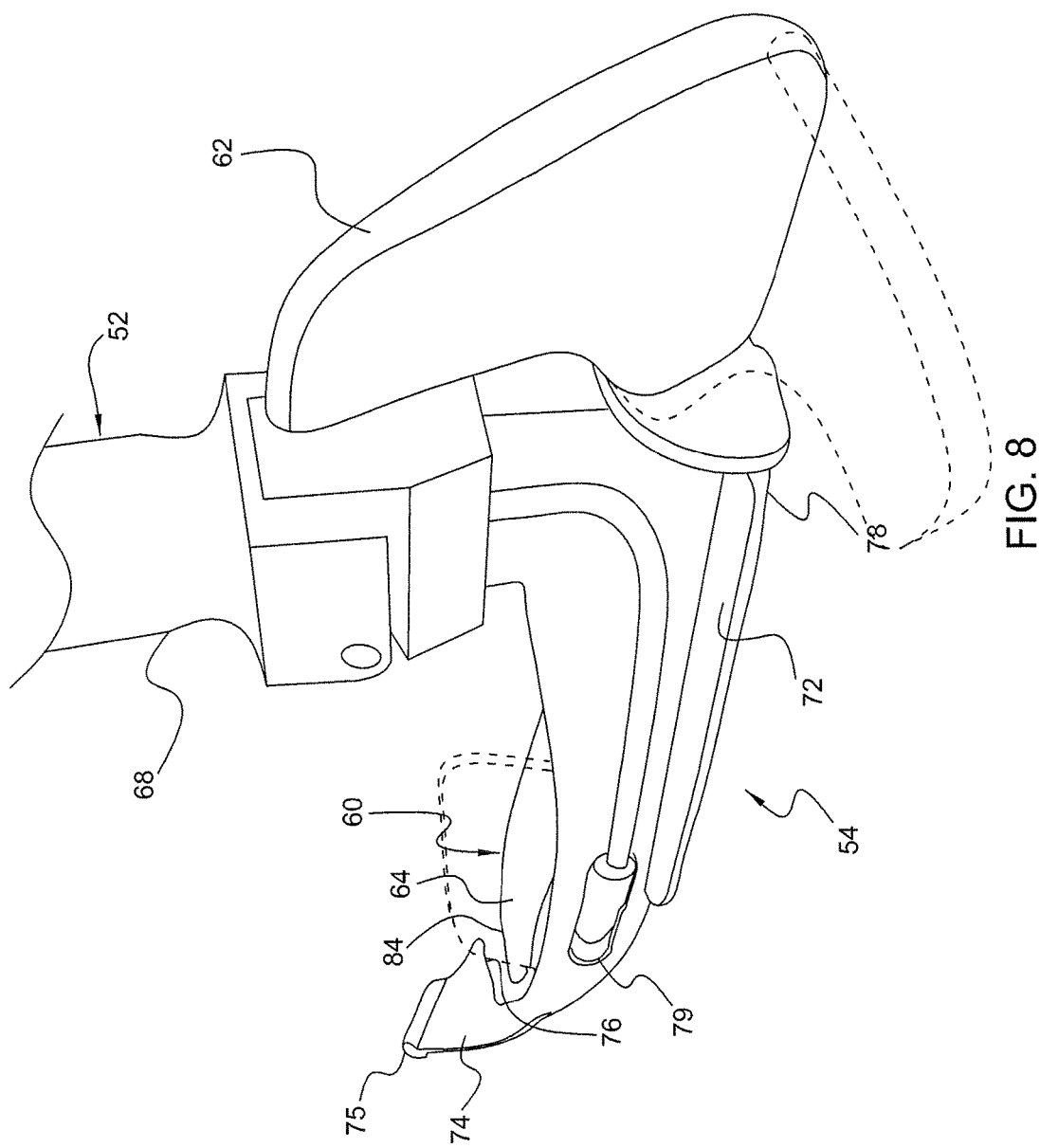
FIG. 8 is a rear left perspective view of the laryngoscope as shown in FIG. 1 with the portion of the blade shown in the first position and the second pivoted position depicted in dashed lines.
Figure 9:
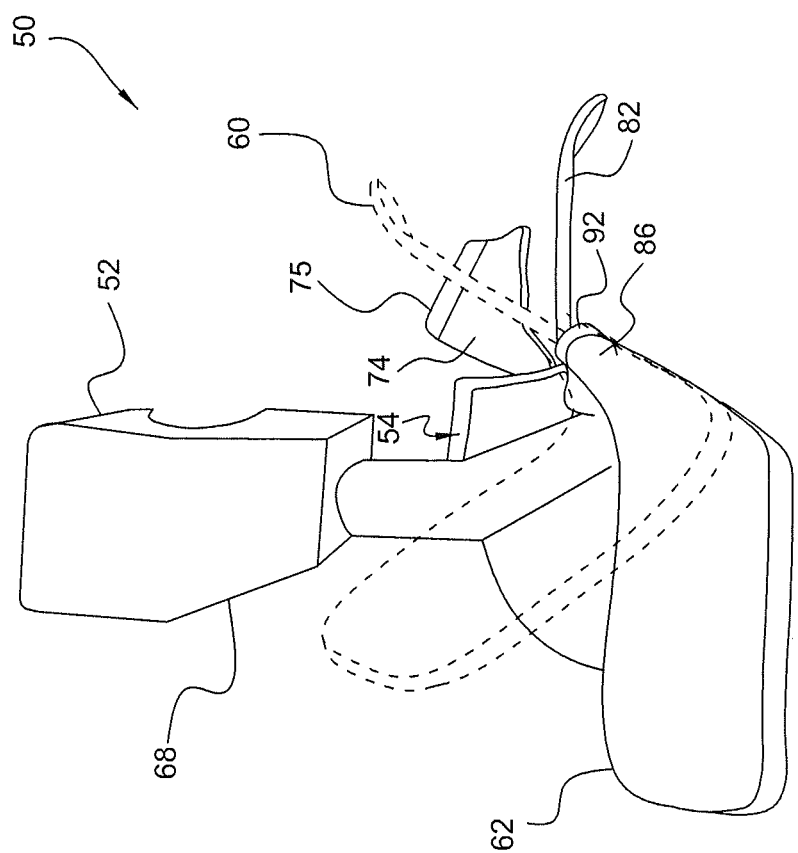
FIG. 9 is a rear elevation view of the laryngoscope as shown in FIG. 1 with the portion of the blade shown in the first position and the second pivoted position depicted in dashed lines.

Means are provided for actuating the pivotal movement of the tongue deflector 60. In one embodiment, an end wall 94 at the proximal end 78 of the blade 54 defines a hole 95 for passing the rod 86 (FIGS. 7-9). The actuating means comprises the lever 62, which is integral with the proximal end of the rod 86. The tongue deflector 60 is pivoted by manually rotating the lever 62 relative to the blade 54, which simultaneously rotates the rod 86 within the sleeves 92 and the connected tongue deflector 60. A pivoting force can be easily transmitted to the tongue deflector 60 using the lever 62 by the action of the fingers in turning the wrist. This allows the tongue of the patient to be lifted or swept aside to expose the glottis.

It is understood that other suitable means are possible for rotating the tongue deflector 60 relative to the blade 54. For example, an automated mechanism may be used for rotation of the tongue deflector 60, such as an electric or pneumatic motor driver activating a mechanical device. Alternatively, the lever 62 can be connected to an actuation means mechanically or electrically, such as by a programmable logic controller (PLC) or controller with logic to determine which functions to execute to actuate the tongue deflector 60.

In one embodiment, the end wall 94 may be adapted to fixedly receive the lever 62 so as to maintain the relative position of the blade 54 and the tongue deflector 60 in the relative angular position. More particularly, the end wall 94 may comprise a locking mechanism having a slot 96 adjacent to, and along the path of, the rotating lever 62. One end 98 of the slot 96 corresponds to the home position of the tongue deflector 60. A second end 100 of the slot 96 corresponds to the angular position of the tongue deflector 60 relative to the blade 54. The locking mechanism maintains the tongue deflector 60 in a desired angular position relative to the blade 54 by locking in position the lever 62 and integral rod 86. The tongue deflector 60 thus remains in relative angular position without requiring the hands of the user. Removing the lever 62 from the second end 100 of the slot 96 releases the lever 62 and allows the tongue deflector 60 to return to the original home position in the recess 76 flush with edge and the distal end 75 of the blade 54.

In use, the user is typically working from a position above the head of a supine patient. The head of the patient is stabilized and the mouth is opened. For a right-handed user, the handle 52 of the laryngoscope 50 is usually held vertically in the left hand with the blade 54 oriented downwards and away from the user. The blade 54 is inserted into the mouth of the patient until the distal end of the blade 54 is positioned at the junction between the base of the tongue and the base of the epiglottis. The angled distal end 75 of the blade 54 serves to elevate the tissue at the base of the tongue, including the epiglottis, which helps the user visualize the glottic opening.

The rigid distal end 75 of the blade 54 of the laryngoscope is configured to allow for easy insertion and engagement of the laryngoscope blade under the tongue for exposure of the glottis. This rigid distal tip also allows for easier engagement of the vallecula, stretching the tissue at the base of the tongue and resultant easier lifting of the epiglottis. In this position, with one hand holding the handle 52 of the laryngoscope 50, the user rotates the lever 62 for pivoting the tongue deflector 60 using the thumb or fingers of the other hand. Rotating the lever 62 relative to the blade 54 rotates the rod 62 and connected tongue deflector 60 about their rotation axis causing the tongue deflector 60 to assume an angular position with respect to the blade 54. This action of the tongue deflector 60 elevates and sweeps the tongue and exposes the glottis.

If desired, the lever 62 is engaged in the second end 100 of the slot 96 in the end wall 94 of the blade 54 for locking the tongue deflector 60 in place. In one embodiment, as the lever 62 the end of the slot 96 at the fully rotated position of the tongue deflector 60, the lever 62 seats in the opening 100 in the end wall 94 to lock the tongue deflector 60 in the angular position. Thus, the tongue is held and kept in a position from the posterior pharynx until the lever 62 is disengaged. The tongue deflector 60 functions to hold back tissue that would otherwise obscure the vision of the user and block the airway, as well as maintaining airway patency. The user may then leave the laryngoscope 50 in a condition with the tongue deflector 60 locked in the relative angular position and intubate the patient. The larynx is visualized off the medial side of the laryngoscope blade 54 where the endotracheal tube or other instruments can be introduced. The tongue deflector 60 will remain locked in the angular position until the end of the lever 62 is released from the second opening 100, allowing the tongue deflector 60 to return to the home position flush with the blade 54.

The laryngoscope 50 having a distal end 75 of the blade 54 angled in a direction opposite to the insertion direction and curved upwards, in essence, eliminates counter rotation and engaging of the base of the vallecula in its entirety while stretching of the Hyoepiglottic ligament. This has the effect of better and deeper engagement, less tissue damage and better lifting and stretching of the tongue tissue at the base of the tongue. The shape of the tongue deflector 60 allows the tongue deflector 60 to engage and sweep the tissue mass of the tongue compressed by the blade 54 during axial rotation. The overall effect is a lifting of the engaged tissue facilitating blade insertion, sweeping of the tongue and visualization of the glottic opening as necessary for airway control intubation.

In one embodiment, the blade 54 including the tongue deflector 60 can be supplied as a sterile packaged, disposable item for single use. In an alternate embodiment, the blade 54 would be constructed for repeated use and to resist degradation from repeated gas, chemical, or steam autoclave sterilization exposures.

The laryngoscope 50 described and shown herein has many advantages, including requiring less force for positioning and movement of the blade as compared to a conventional laryngoscope. Facilitating the sweeping of the tongue is achieved by applying a rotary force from outside of the oral cavity to the tongue deflector 60 for moving the comparatively large tongue muscle mass, which allows a user to engage and sweep the tongue in a manner that is not possible using conventional laryngoscopes. In addition, the locking function of the laryngoscope 50 maintains continued airway patency once established.

As described above, the new blade can be used with conventional laryngoscope handles, which provide both ergonomic and power supply functions. Moreover, the tongue deflector 60 can be made compatible for use on any type of laryngoscope blade known in the art, including Macintosh (curved) blades and Miller (straight) blades, which may be modified for the purposes and function as described herein. The laryngoscope 50 is suitable for use by physicians, especially by anesthetists in procedures requiring the tracheal intubation of patients. The laryngoscope may also be used in veterinary practice. The tongue deflector 60 may also be used with instruments other than a laryngoscope, such as an oral pharyngeal airway.

Referring now to FIGS. 11-20, there is shown an intubation instrument comprising at least a portion of an embodiment of a laryngoscope generally designated at 150. One example of an intubation instrument for use in the present application is described in U.S. Pat. No. 6,543,447, issued Apr. 8, 2003, the contents of which are hereby incorporated by reference in their entirety.

In accordance with one embodiment, the intubation instrument 150 comprises an elongated generally arcuate body 152 including an integral distal blade portion 154. The instrument 150 may be constructed of metal or metal alloys that are capable of repeated use and for withstanding sterilization between uses. Suitable metal or metal alloys include stainless steel or aluminum. Alternatively, the blade 54 may be constructed of any rigid plastic or other composite that is suitable for medical use, or other low cost, sterile material, and may be provided as a single-use, disposable unit. It is understood that the blade 154 may also be made wholly or in part of any material known in the art.

The body 152 is sized and shaped to engage, lift and support the patient's epiglottis to thereby expose the glottis. A distal end 156 of the instrument 150 is inserted into the mouth of a patient. Following insertion, the instrument 150 can provide a path for guiding movement of an endotracheal tube (not shown) in a manner that permits the distal end of the endotracheal tube to move relative to the instrument 150 directly toward the glottis. More particularly, the body 152 of the instrument 150 is configured to define a guide path for advancing the endotracheal tube relative to the inserted instrument 150. The guide path may include an anterior surface of the body 152.

The body 152 of the instrument 150 may further define a passage into which a video scope (not shown) is mounted. Alternatively, a viewing device, such as a Charged Coupled Device ("CCD") or Complementary Metal Oxide Semiconductor ("CMOS") camera may be operably secured to the instrument 150. The camera is selectively positioned near the distal end 156 of the body 152 to provide a perspective view toward the distal end 156 and the surrounding area. Preferably, the camera is secured within a sealed chamber within the body 152, thereby protecting it from water, gasses, and chemicals used in sterilization procedures. Preferably, the CMOS or CCD camera body is also sealed. Lights, which are preferably light emitting diode ("LED") units, may also be positioned toward the distal end 156 of the body 152 to facilitate viewing. The arrangement of the guide path, the passage and the viewing devices ensures that the distal end 156 of the body 152 and the tube remain observable as it is advanced to the glottis. A display may be detached and remote from, or attached to, the instrument 150.

The instrument 150 further comprises a movable tongue deflector 160 pivotally attached to the body 152. The tongue deflector 160 may be formed from the same material as the instrument 150, or another substantially rigid material to allow adequate physical retraction of anatomic structures for proper use. The instrument 150 and tongue deflector 160 may comprise a range of sizes and be suitable for use with adults, children or neonates, as well as being suitable for use in veterinary practice. The overall geometry between the body 152 and the tongue deflector 160 is important for effective operation of the instrument 150. Proportionately smaller sizes should be used for pediatric applications.

The tongue deflector 160 is generally rectangular and has a proximal end 162 and a distal end 164. The tongue deflector 160 is arcuate along its length between the ends such that the surface of the tongue deflector 160 extends in a substantially smooth transition into the blade portion 154 of the body 152 of the instrument 150. Specifically, in a first, home position of the tongue deflector 160, a tongue-contacting surface 166 surface of the tongue deflector 160 is substantially flush with the anterior surface of the body 152. In this configuration, the surface of the tongue deflector 160 is shaped so as to provide surface continuity with the body 152 when the tongue deflector 160 is in the home position. In this arrangement, the tongue deflector 160 provides no greater bulk that might obstruct either the visual field or working access distal to the tongue deflector 160 during an intubation procedure.

The tongue deflector 160 is pivotally mounted to the body 152 so that the tongue deflector 160 may be selectively angularly positioned with respect to the blade portion 154 of the body 152 by means of an operating lever 172 manipulated by the user. Displacement of the tongue deflector 160 causes the tongue-contacting surface 166 of the tongue deflector 160 to execute a tongue deflecting movement for exposing the glottis. More particularly, a rod 168 extends from the lever 172 and is fastened along the inner edge of the inner surface of the tongue deflector 160 for rotation of the tongue deflector 160 with the lever 172. The rod 168 is journaled in at least one tubular sleeve 170 fixed to the inner surface of the body 152. This arrangement allows the tongue deflector 160 and the rod 168 to pivot freely with respect to the body 152 about a rotation axis. The tongue deflector 160 can thus articulate, which means movement upward, downward, or in a circular or elliptical path, along or about the axis of rotation. It is understood that the tongue deflector 160 may be pivotally mounted to the body 152 by any conventional means, such as ball and socket joints, hinges, straps, and the like.

Means are provided for actuating the pivotal movement of the tongue deflector 160. The actuating means comprises the lever 172, which is integral with the proximal end of the rod 168. The tongue deflector 160 is pivoted by manually rotating the lever 172 relative to the body 152, which simultaneously rotates the rod 168 within the sleeves 170 and the connected tongue deflector 160. A pivoting force can thus be easily transmitted to the tongue deflector 160 using the lever 172 by the action of the fingers in turning the wrist. This allows the tongue of the patient to be lifted or swept aside to expose the larynx.

Another embodiment of a movable tongue deflector is shown in FIGS. 21-26 and generally designated at 260. The tongue deflector 260 is generally rectangular and has a proximal end 262 and a distal end 264. The tongue deflector 260 is arcuate along its length between the ends such that the surface of the tongue deflector 260 extends in a substantially smooth transition into the blade portion 254 of the body 252 of the instrument 150. The tongue deflector comprises an arcuate distal tip 270. In a first, home position of the tongue deflector 260, a tongue-contacting surface 266 surface of the tongue deflector 260 is substantially flush with the anterior surface of the body 152 of the instrument 150. In this configuration, the surface of the tongue deflector 260 is shaped so as to provide surface continuity with the body 152 when the tongue deflector 260 is in the home position. In this arrangement, the tongue deflector 260 provides no greater bulk that might obstruct either the visual field or working access distal to the tongue deflector 260 during an intubation procedure.

In this embodiment, the operating lever 172 is connected to the rod 168, which extends from the lever 172 positioned adjacent the proximal end of the body 152. The distal end of the rod 168 is connected via a ball joint 280 for rotation with a rotating lever 282 fastened along the inner edge of the inner surface of the tongue deflector 260 for rotation of the tongue deflector 160 with the lever 172. The rod 168 is journaled in at least one tubular sleeve 170 fixed to the inner surface of the body 152. This arrangement allows the tongue deflector 260 to pivot freely with respect to the body 152 about a rotation axis while allowing convenient access to the operating lever 172 for the user. The tongue deflector 260 can thus articulate, which means movement upward, downward, or in a circular or elliptical path, along or about the axis of rotation. It is understood that the tongue deflector 260 may be pivotally mounted to the body 152 by any conventional means, such as ball and socket joints, hinges, straps, and the like.

Accordingly, in this embodiment, means provided for actuating the pivotal movement of the tongue deflector 260 comprises the lever 172, which is integral with the proximal end of the rod 168, the ball joint 280 and the lever 282. The tongue deflector 260 is pivoted by manually rotating the lever 172 relative to the body 152, which simultaneously rotates the rods 168, 182 within the sleeves 170 and the connected tongue deflector 260. A pivoting force can thus be easily transmitted to the tongue deflector 260 using the lever 172 by the action of the fingers in turning the wrist. This allows the tongue of the patient to be lifted or swept aside to expose the larynx.

It is understood that other suitable means are possible for rotating the tongue deflector 260 relative to the blade 154. For example, an automated mechanism may be used for rotation of the tongue deflector 260, such as an electric or pneumatic motor driver activating a mechanical device. Alternatively, the lever 172 can be connected to an actuation means mechanically or electrically, such as by a programmable logic controller (PLC) or controller with logic to determine which functions to execute to actuate the tongue deflector 260.

In another embodiment, a fitted transparent protective sheath (not shown) may be positioned substantially over the body 152 of the instrument 150 to facilitate cleaning and provide sterile multiple use of the instrument 150. Preferably, the sheath is a transparent polymer, such as plastic, which sheds mucus and blood, has little tendency to fog during use, and equilibrates rapidly to airway temperature. In particular, the sheath may be tightly fitted over the lens of the camera to prevent an encumbered view.

In use, the user is typically working from a position above the head of a supine patient. The head of the patient is stabilized and the mouth is opened. For a right-handed user, the laryngoscope 50 is usually held vertically in the left hand, with the distal end 56 of the body 52 oriented downwards and away from the user. The body 52 is inserted into the mouth until the distal end 56 of the body 52 is positioned at the junction between the base of the tongue and the base of the epiglottis.

With one hand holding the laryngoscope 150, the user rotates the lever 172 for pivoting the tongue deflector 160, 260 using the thumb or fingers of the other hand. When the lever 172 is rotated relative to the body 152, the rod 168 and connected tongue deflector 160, 260 are rotated about their rotation axis, causing the tongue deflector 160, 260 to assume an angular position with respect to the blade 154 of the body 152. This action elevates and sweeps the tongue and exposes the larynx. The tongue deflector 160, 260 functions to hold back tissue that would otherwise obscure the vision of the user and block the airway as well as maintaining airway patency. The user may then intubate the patient. The larynx is visualized off the medial side of the body 152 where the endotracheal tube or other instruments can be introduced. The tongue deflector 160, 260 can be released from the angular position, allowing the tongue deflector 160, 260 to return to the home position flush with the anterior surface of the body 152.

The present intubation instrument includes a number of features that greatly increase the ease with which the instrument and endotracheal tube can be properly located and continuously observed via a video scope or other optic device. The overall effect is facilitated insertion, sweeping and visualization of the glottic opening as necessary for intubation.

In one embodiment, the intubation instrument 150, including the tongue deflector 160, 260 would be supplied as a sterile packaged, disposable item for single use. In an alternate embodiment, the instrument 150 would be constructed for repeated use and to resist degradation from repeated gas, chemical, or steam autoclave sterilization exposures.

The laryngoscope 150 described and shown herein has many advantages, including requiring less force for positioning and movement as compared to a conventional laryngoscope. Facilitating this sweeping of the tongue is achieved by applying a rotary force to the tongue deflector 160, 260 for moving the comparatively tongue muscle mass. The tongue deflector 160, 260 allows a user to engage the tongue in a manner that is not possible using conventional laryngoscopes. Precious time is saved without the need to reposition the blade to engage the tongue from a different angle to expose the airway opening. Less cervical spine manipulation can be achieved by reducing the lift often needed on the tongue and lower mandible to expose the glottis opening.

As described above, the tongue deflector 160, 260 can be used with other conventional intubation instruments, which provide both ergonomic and viewing device functions. Moreover, the tongue deflector 160, 260 can be made compatible for use on any type of laryngoscope video scope blades, which may be modified for the purposes and function as described herein. The laryngoscope 150 is suitable for use by physicians, especially by anesthetists in procedures requiring the tracheal intubation of patients. The laryngoscope may also be used in veterinary practice. The tongue deflector 160, 260 may also be used with instruments other than a laryngoscope, such as an oral pharyngeal airway and endoscopy equipment.

Although the present laryngoscope has been shown and described in considerable detail with respect to only a few exemplary embodiments thereof, it should be understood by those skilled in the art that I do not intend to limit the laryngoscope to the embodiments since various modifications, omissions and additions may be made to the disclosed embodiments without materially departing from the novel teachings and advantages, particularly in light of the foregoing teachings. Accordingly, I intend to cover all such modifications, omission, additions and equivalents as may be included within the spirit and scope of the laryngoscope as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. A device for inserting into a mouth of a patient having a tongue for intubating the patient, the intubation device comprising:
   a tubular handle;
   an arcuate tubular blade integral with the handle, the blade including
      a stationary portion having a longitudinal axis and an upper surface, and
      a movable portion having an upper surface for engaging the tongue of the patient, the movable portion mounted to the stationary portion of the blade for rotation about an axis substantially parallel to the longitudinal axis of the stationary portion of the blade from a first position of the movable portion where the upper surface of the movable portion is continuous with the upper surface of the stationary portion; and
   an operating member configured to be manipulated by a user for rotating the movable portion of the blade to a second position relative to the stationary portion of the blade such that the upper tongue engaging surface of the movable portion of the blade moves upwardly from the handle,
wherein intubation of the patient by manipulation of the handle includes at least the rotating motion of the movable portion of the blade for moving the tongue.

2. The laryngoscope as recited in claim 1, wherein the operating member comprises an elongate rod integrally formed with the movable portion of the blade.

3. The laryngoscope as recited in claim 1, wherein the tubular handle comprises means for directing a camera toward a distal end of blade.

* * * * *